(12) United States Patent
Hassibi et al.

(10) Patent No.: US 9,499,861 B1
(45) Date of Patent: Nov. 22, 2016

(54) METHODS AND SYSTEMS FOR MULTIPLEX QUANTITATIVE NUCLEIC ACID AMPLIFICATION

(71) Applicant: INSILIXA, INC., Sunnyvale, CA (US)

(72) Inventors: Arjang Hassibi, Santa Clara, CA (US); Kshama Jirage, Palo Alto, CA (US); Arun Manickam, Santa Clara, CA (US); Rituraj Singh, Santa Clara, CA (US)

(73) Assignee: InSilixa, Inc., Sunnyvale, CA (US)

( * ) Notice: Subject to any disclaimer, the term of this patent is extended or adjusted under 35 U.S.C. 154(b) by 0 days.

(21) Appl. No.: 14/850,659

(22) Filed: Sep. 10, 2015

(51) Int. Cl.
*C12Q 1/68* (2006.01)

(52) U.S. Cl.
CPC .................................. *C12Q 1/686* (2013.01)

(58) Field of Classification Search
None
See application file for complete search history.

(56) References Cited

U.S. PATENT DOCUMENTS

| | | | |
|---|---|---|---|
| 4,027,971 A | 6/1977 | Kolman et al. |
| 4,469,863 A | 9/1984 | Ts'o et al. |
| 4,539,295 A | 9/1985 | Blough, Jr. |
| 5,034,506 A | 7/1991 | Summerton et al. |
| 5,210,015 A | 5/1993 | Gelfand et al. |
| 5,216,141 A | 6/1993 | Benner |
| 5,235,033 A | 8/1993 | Summerton et al. |
| 5,323,115 A | 6/1994 | Werner, Jr. |
| 5,386,023 A | 1/1995 | Sanghvi et al. |
| 5,455,705 A | 10/1995 | Gusinov |
| 5,487,972 A | 1/1996 | Gelfand et al. |
| 5,538,848 A | 7/1996 | Livak et al. |
| 5,599,668 A | 2/1997 | Stimpson et al. |
| 5,602,240 A | 2/1997 | De Mesmaeker et al. |
| 5,637,684 A | 6/1997 | Cook et al. |
| 5,644,048 A | 7/1997 | Yau |
| 5,674,698 A | 10/1997 | Zarling et al. |
| 5,925,519 A | 7/1999 | Jensen et al. |
| 5,994,056 A | 11/1999 | Higuchi |
| 6,048,690 A | 4/2000 | Heller et al. |
| 6,083,763 A | 7/2000 | Balch |
| 6,103,476 A | 8/2000 | Tyagi et al. |
| 6,110,426 A | 8/2000 | Shalon et al. |
| 6,174,670 B1 | 1/2001 | Wittwer et al. |
| 6,312,906 B1 | 11/2001 | Cass et al. |
| 6,330,092 B1 | 12/2001 | Aronson |
| 6,365,729 B1 | 4/2002 | Tyagi et al. |
| 6,469,524 B1 | 10/2002 | Oberdier |
| 6,472,887 B1 | 10/2002 | Tullis et al. |
| 6,516,276 B1 | 2/2003 | Ghandour et al. |
| 6,593,091 B2 | 7/2003 | Keys et al. |
| 6,673,536 B1 | 1/2004 | Stoughton et al. |
| 6,724,324 B1 | 4/2004 | Lambert |
| 6,744,502 B2 | 6/2004 | Hoff et al. |
| 7,145,645 B2 | 12/2006 | Blumenfeld et al. |
| 7,361,472 B2 | 4/2008 | Yguerabide et al. |
| 7,463,353 B2 | 12/2008 | Yershov |
| 7,504,832 B2 | 3/2009 | Kandori et al. |
| 7,599,060 B2 | 10/2009 | Hoshizaki et al. |
| 7,630,227 B2 | 12/2009 | Tran |
| 7,995,679 B2 | 8/2011 | Ranganathan et al. |
| 8,048,626 B2 | 11/2011 | Hassibi et al. |
| 8,517,329 B2 | 8/2013 | Nash et al. |
| 8,518,329 B2 | 8/2013 | Hassibi et al. |
| 8,637,436 B2 | 1/2014 | Hassibi |
| 8,735,067 B2 * | 5/2014 | Zhang .................... C12Q 1/686 435/6.12 |
| 8,969,781 B2 | 3/2015 | Hassibi et al. |
| 9,133,504 B2 | 9/2015 | Hassibi et al. |
| 9,223,929 B2 | 12/2015 | Hassibi et al. |
| 9,341,589 B2 | 5/2016 | Hassibi et al. |
| 2002/0001844 A1 | 1/2002 | Frutos et al. |
| 2002/0106653 A1 | 8/2002 | Kurane et al. |
| 2002/0146745 A1 | 10/2002 | Natan et al. |
| 2003/0040000 A1 | 2/2003 | Connolly et al. |
| 2003/0071843 A1 | 4/2003 | Hoff et al. |
| 2003/0143591 A1 | 7/2003 | Davies et al. |
| 2003/0186310 A1 | 10/2003 | Kincaid |
| 2003/0225718 A1 | 12/2003 | Shmulevich et al. |
| 2004/0053254 A1 * | 3/2004 | Wangh .................... C07H 21/00 435/6.1 |
| 2004/0080629 A1 | 4/2004 | Sato et al. |
| 2004/0265902 A1 | 12/2004 | Fricker et al. |
| 2005/0089924 A1 | 4/2005 | Ho et al. |
| 2006/0014151 A1 | 1/2006 | Ogura et al. |
| 2006/0068378 A1 | 3/2006 | Mirkin et al. |
| 2006/0078929 A1 | 4/2006 | Bickel et al. |
| 2006/0088844 A1 | 4/2006 | Xu |
| 2006/0123516 A1 | 6/2006 | Ronen et al. |
| 2006/0208254 A1 | 9/2006 | Goodman et al. |
| 2006/0269922 A1 | 11/2006 | Sagner et al. |
| 2007/0026421 A1 | 2/2007 | Sundberg et al. |
| 2007/0065818 A1 | 3/2007 | Foti et al. |

(Continued)

FOREIGN PATENT DOCUMENTS

| | | |
|---|---|---|
| WO | WO 02/099397 A2 | 12/2002 |
| WO | WO-03062791 A2 | 7/2003 |

(Continued)

OTHER PUBLICATIONS

Lalkhen (Clinical tests: sensitivity and specificity, Contin Educ Anaesth Crit Care Pain (2008) 8 (6): 221-223, Nov. 6, 2008).*

Sanchez et al. (Linear-After-The-Exponential (LATE)-PCR: An advanced method of asymmetric PCR and its uses in quantitative real-time analysis, PNAS, vol. 101, No. 7, pp. 1933-1938, Feb. 17, 2004).*

Tomlinson et al. (Influence of the length of target DNA overhang proximal to the array surface on discrimination of single-base mismatches on a 25-mer oligonucleotide array, BMC Res Notes. Apr. 17, 2014;7:251).*

Pont-Kindon et al. (Direct molecular haplotyping by melting curve analysis of hybridization probes: beta 2-adrenergic receptor haplotypes as an example, Nucleic Acids Research, 2005, vol. 33, No. 10, Jun. 3, 2005).*

(Continued)

*Primary Examiner* — Aaron Priest
(74) *Attorney, Agent, or Firm* — Wilson Sonsini Goodrich & Rosati

(57) ABSTRACT

The present disclosure provides methods, devices and systems that enable simultaneous multiplexing amplification reaction and real-time detection in a single reaction chamber.

25 Claims, 19 Drawing Sheets

(56) References Cited

U.S. PATENT DOCUMENTS

| | | | |
|---|---|---|---|
| 2007/0077609 A1 | 4/2007 | Gambhir et al. | |
| 2007/0099198 A1 | 5/2007 | Hassibi et al. | |
| 2007/0212681 A1 | 9/2007 | Shapiro et al. | |
| 2007/0218610 A1 | 9/2007 | Lim et al. | |
| 2008/0039339 A1 | 2/2008 | Hassibi et al. | |
| 2008/0081769 A1* | 4/2008 | Hassibi | C40B 30/04 506/9 |
| 2008/0085839 A1 | 4/2008 | Klapproth | |
| 2008/0176757 A1* | 7/2008 | Hassibi | C12Q 1/6851 506/9 |
| 2008/0305481 A1* | 12/2008 | Whitman | C12Q 1/6818 435/6.12 |
| 2009/0111207 A1 | 4/2009 | Choumane et al. | |
| 2009/0137418 A1 | 5/2009 | Miller et al. | |
| 2009/0156415 A1* | 6/2009 | Remacle | C12Q 1/6837 506/9 |
| 2009/0325164 A1 | 12/2009 | Vossenaar et al. | |
| 2010/0041030 A1 | 2/2010 | Hartwich | |
| 2010/0105033 A1 | 4/2010 | Sun et al. | |
| 2010/0122904 A1 | 5/2010 | Hassibi et al. | |
| 2010/0300899 A1 | 12/2010 | Levine et al. | |
| 2010/0330578 A1 | 12/2010 | Duhr et al. | |
| 2011/0086361 A1* | 4/2011 | Klunder | C12Q 1/6834 435/6.12 |
| 2011/0312810 A1 | 12/2011 | Moini et al. | |
| 2012/0040853 A1* | 2/2012 | Pierik | C12Q 1/6851 506/9 |
| 2012/0052563 A1 | 3/2012 | Liang et al. | |
| 2012/0077692 A1 | 3/2012 | Hassibi et al. | |
| 2012/0088682 A1 | 4/2012 | Rothberg et al. | |
| 2012/0094298 A1* | 4/2012 | Seul | C12Q 1/6865 435/6.12 |
| 2012/0115214 A1 | 5/2012 | Battrell et al. | |
| 2012/0168306 A1 | 7/2012 | Hassibi et al. | |
| 2013/0210656 A1 | 8/2013 | Wangh et al. | |
| 2013/0225441 A1 | 8/2013 | Hassibi | |
| 2013/0252827 A1* | 9/2013 | Chun | C12Q 1/6818 506/2 |
| 2013/0345065 A1 | 12/2013 | Hassibi et al. | |
| 2014/0001341 A1 | 1/2014 | Hassibi et al. | |
| 2014/0011710 A1 | 1/2014 | Hassibi et al. | |
| 2014/0318958 A1 | 10/2014 | Hassibi et al. | |
| 2014/0363821 A1 | 12/2014 | Bashir et al. | |
| 2015/0093849 A1 | 4/2015 | Shepard et al. | |
| 2015/0125855 A1 | 5/2015 | Li et al. | |
| 2016/0160271 A1 | 6/2016 | Hassibi et al. | |

FOREIGN PATENT DOCUMENTS

| | | |
|---|---|---|
| WO | WO 2004/011144 A2 | 2/2004 |
| WO | WO 2004/059006 A1 | 7/2004 |
| WO | WO 2005/118870 A2 | 12/2005 |
| WO | WO 2005/121159 A1 | 12/2005 |
| WO | WO 2006/014351 A2 | 2/2006 |
| WO | WO 2006/037527 A1 | 4/2006 |
| WO | WO 2006/053769 A1 | 5/2006 |
| WO | WO 2008/143646 A2 | 11/2008 |

OTHER PUBLICATIONS

Liu et al. (TaqMan probe array for quantitative detection of DNA targets, Nucleic Acids Res. 2006; 34(1): e4. Published online Jan. 10, 2006).*

Zhu et al. (Multiplex Asymmetric PCR-Based Oligonucleotide Microarray for Detection of Drug Resistance Genes Containing Single Mutations in Enterobacteriaceae, Antimicrob Agents Chemother. Oct. 2007; 51(10): 3707-3713. Published online Jul. 23, 2007).*

Lee, et al. Seven-color, homogeneous detection of six PCR products. Biotechniques. Aug. 1999;27(2):342-9.

Beaucage, et al. The functionalization of oligonucleotides via phosphoramidite derivatives. Tetrahedron 49.10 (1993): 1925-1963.

Brill, et al. Synthesis of oligodeoxynucleoside phosphorodithioates via thioamidites. Journal of the American Chemical Society, 1989, 111(6), 2321-2322.

Canon. High resolution thermal melt analysis. http://culs.canon.com/Science/Technology_Overview/High_Resolution_thermal_melt_analysis/High_Resolution_Thermal_Melt_Analysis.shtml. Accessed on Jun. 10, 2015. 1 pg.

Carlsson, et al. Screening for genetic mutations. Nature. Mar. 21, 1996;380(6571):207.

Cronin, et al. Cystic fibrosis mutation detection by hybridization to light-generated DNA probe arrays. Hum Mutat. 1996;7(3):244-55.

De Mesmaeker, et al. Comparison of rigid and flexible backbones in antisense oligonucleotides. Bioorganic & Medicinal Chemistry Letters, 1994 4(3), 395-398.

Denpcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.

Dolganov, et al. Novel molecular diagnostic (MDx) Platform for Highly-Multiplex Drug Susceptibility Testing of M. tuberculosis. http://www.stoptb.org/wg/new_diagnostics/assets/documents/09-NDWG-Annual-Meeting_GarySCHOOLNIK_&_Gregory_DOLGANOV.pdf. Accessed on Jun. 10, 2015. 13 pgs.

Eckstein. Oligonucleotides and Analogues: A Practical Approach. Press at Oxford University Press, 1991: 313.

Falconnet, et al. Rapid, sensitive and real-time multiplexing platform for the analysis of protein and nucleic-acid biomarkers. Anal Chem. Feb. 3, 2015;87(3):1582-9. doi: 10.1021/ac502741c. Epub Jan. 21, 2015.

FDA. Response to Section 501(k) Premarket Notification of Intent to Market. Re: K143178. Dated Jan. 30, 2015. 9 pages.

Gao, et al. Unusual Conformation of a 3'-thioformacetal Linkage in a DNA Duplex. Journal of biomolecular NMR, 1994, 4(1), 17-34.

Hassibi, et al. Real-time DNA microarray analysis. Nucleic Acids Res. Nov. 2009;37(20):e132. doi: 10.1093/nar/gkp675. Epub Aug. 31, 2009.

Hassibi. CMOS Biochips for Point-of-Care Molecular Diagnostics. Hot Chips—Aug. 2014. 32 pgs.

Horn, et al. Oligonucleotides with alternating anionic and cationic phosphoramidate linkages: synthesis and hybridization of stereouniform isomers. Tetrahedron letters,1996, 37(6), 743-746.

IDT—Integrated DNA Technologies. Strategies for Attaching Oligonucleotides to Solid Supports. Copyright 2014 (v3). Aug. 10, 2011. 7pages.

Jenkins, et al.The biosynthesis of carbocyclic nucleosides. Chem. Soc. Rev., 1995, 24(3), 169-176.

Khabzaoui, et al. A multicriteria genetic algorithm to analyze microarray data. In Evolutionary Computation, Jun. 2004. CEC2004. Congress on vol. 2, pp. 1874-1881. IEEE.

Kiedrowski, et al. Parabolic Growth of a Self-Replicating Hexadeoxynucleotide Bearing a 3'-5'-Phosphoamidate Linkage. Angewandte Chemie International Edition in English, 1991, 30(4), 423-426.

Lalkhen, et al. Clinical tests: sensitivity and specificity. Continuing Education in Anaesthesia, Critical Care & Pain. 2008. 8(6), 221-223.

Letsinger, et al. Cationic oligonucleotides. Journal of the American Chemical Society, 1988 110(13), 4470-4471.

Letsinger, et al. Hybridization of alternating cationic/anionic oligonucleotides to RNA segments. Nucleosides, Nucleotides & Nucleic Acids 13.6-7 (1994): 1597-1605.

Li, et al. Bead-Based Melting Analysis in Temperature-Graident Microchannels for Single Nucleotide Polymorphisms Detection. 17th International Conference on Miniaturized Systems for Chemistry and Life Sciences. Oct. 27-31, 2013. Freiburg, Germany. 3 pages.

Metzker. Sequencing technologies—the next generation. Nat Rev Genet. Jan. 2010;11(1):31-46. doi: 10.1038/nrg2626. Epub Dec. 8, 2009.

Nanogen. A chip-based genetic detector for rapid identification of individuals. National institute of justice—Project No. 97-LB-VX-0004. Apr. 2006. 102 pgs.

(56) References Cited

OTHER PUBLICATIONS

Pont-Kindon, et al. Direct molecular haplotyping by melting curve analysis of hybridization probes: beta 2-adrenergic receptor haplotypes as an example. Nucleic Acids Res. Jun. 3, 2005;33(10):e89.
Pourmand, et al. Direct electrical detection of DNA synthesis. Proc Natl Acad Sci U S A. Apr. 25, 2006;103(17):6466-70. Epub Apr. 13, 2006.
Rothe, et al. Multi-target electrochemical biosensing enabled by integrated CMOS electronics. Journal of Micromechanics and Microengineering, 2011, 21(5), 054010.
Salm, et al. Ultralocalized thermal reactions in subnanoliter droplets-in-air. Proc Natl Acad Sci U S A. Feb. 26, 2013;110(9):3310-5. doi: 10.1073/pnas.1219639110. Epub Feb. 11, 2013.
Sanghvi, et al. Chapters 2 and 3, ASC Symposium Series 580, "Carbohydrate Modifications in Antisense Research", 1994.
Sanghvi, et al. Chapters 6 and 7, ASC Symposium Series 580, "Carbohydrate Modifications in Antisense Research", 1994.
Savyon Diagnostics. Nano CHIP. www.nanochip400.com. NG Jun. 2010—VER1. 8pgs.
Scherf, et al. Letter from Uwe Scherf-S to Kristen Kanack re: K143178 Section 510(k). Department of Health & Human Services. Jan. 30, 2015. 9pgs.
Sosnowski. A chip-based genetic detector for rapid identification of individuals Document No. 213911. Award No. 1997-LB-XV-0004. Apr. 2006. 100 pages.
Stimpson, et al. Real-time detection of DNA hybridization and melting on oligonucleotide arrays by using optical wave guides. Proc Natl Acad Sci U S A. Jul. 3, 1995;92(14):6379-83.
Stochastic Matrix, one page, 2013. Wolfram MathWorld. Obtained online on May 29, 2013.
Vikalo, et al. A statistical model for microarrays, optimal estimation algorithms, and limits of performance. Signal Processing, IEEE Transactions on, 2006, 54(6), 2444-2455.
Vikalo, et al. Optimal estimation of gene expression levels in microarrays. Presented at the IEEE Int. Workshop Genomic Signal Processing Statistics, Newport, RI, May 22-24, 2005.
Vikalo, et al. Proof of publication date of [Vikalo, et al. Optimal estimation of gene expression in microarrays.] as Mar. 5, 2005, one page, acquired from USPTO Library on Jun. 13, 2014.
Yuen, et al. Accuracy and calibration of commercial oligonucleotide and custom cDNA microarrays. Nucleic Acids Res. May 15, 2002;30(10):e48.
Zhang. Noisy Data with Outliers, one page, 1996. Obtained online on Feb. 9, 2013.
Matsubara, et al. On-chip nanoliter-volume multiplex TaqMan polymerase chain reaction from a single copy based on counting fluorescence released microchambers. Anal Chem. Nov. 1, 2004;76(21):6434-9.
Reed, et al. High-resolution DNA melting analysis for simple and efficient molecular diagnostics. Pharmacogenomics. Jun. 2007;8(6):597-608.
Soon, et al. High Throughput Melting Curve Analysis in Monolithic Silicon-Based Microfluidic Device. 14th International Conference on Miniaturized Systems for Chemistry and Life Sciences. Oct. 3-7, 2010. Groningen, The Netherlands.
Tang, et al. Simple and effective method for generating single-stranded DNA targets and probes. Biotechniques. Jun. 2006;40(6):759-63.
International search report and written opinion dated Jan. 28, 2016 for PCT/US2015/049341.
Singh, et al. A CMOS-Microfluidic Chemiluminescence Contact Imaging Microsystem. IEEE Journal of Solid-State Circuits. Nov. 2012;47(11) 2822-33.
Singh. High Dynamic Range CMOS-Integrated Biosensors. https://repositories.lib.utexas.edu/bitstream/handle/2152/29144/SINGH-DISSERTATION- 2013.pdf?sequence=1. May 1, 2013. Accessed on Feb. 11, 2016. 189 pages.
Brodsky, et al. Identification and handling of artifactual gene expression profiles emerging in microarray hybridization experiments. Nucleic Acids Res. Mar. 3, 2004;32(4):e46.
Held, et al. Modeling of DNA microarray data by using physical properties of hybridization. Proc Natl Acad Sci U S A. Jun. 24, 2003;100(13):7575-80. Epub Jun. 13, 2003.
Co-pending U.S. Appl. No. 14/665,904, filed Mar. 23, 2015.
Co-pending U.S. Appl. No. 15/097,037, filed Apr. 12, 2016.
International Search Report and Written Opinion dated Jul. 15, 2016 for International PCT Patent Application No. PCT/US16/23634.
Marcy, et al. Innovative integrated system for real-time measurement of hybridization and melting on standard format microarrays. Biotechniques. Jun. 2008; 44(7):913-20. doi: 10.2144/000112758.
Meuzelaat, et al. DNA diagnostics by surface-bound melt-curve reactions. J Mol Diagn. Feb. 2007; 9(1):30-41.
Pierik, et al. Rapid genotyping of human papillomavirus by post-PCR array-based hybridization techniques. J Clin Microbiol. Apr. 2011; 49(4):1395-402. doi: 10.1128/JCM.01606-10. Epub Feb. 16, 2011.
Rant, et al. Switchable DNA interfaces for the highly sensitive detection of label-free DNA targets. Proc Natl Acad Sci U.S.A. Oct. 30, 2007; 104(44):17364-9. Epub Oct. 19, 2007.

\* cited by examiner

METHODS AND SYSTEMS FOR MULTIPLEX QUANTITATIVE NUCLEIC ACID AMPLIFICATION

SEQUENCE LISTING

The instant application contains a Sequence Listing which has been submitted electronically in ASCII format and is hereby incorporated by reference in its entirety. Said ASCII copy, created on Oct. 1, 2015, is named 42500-715.601_SL.txt and is 747 bytes in size.

BACKGROUND

Nucleic acid target amplification assays such as polymerase chain reaction process (PCR) can amplify (i.e., replicate) specific sequences of nucleic acids of a DNA template in-vitro. The target amplification assays may become a powerful and widely-used tool in molecular biology and genomics, as they can selectively increase the number of copies of target molecules from a just a few to billions in a matter of hours and thus making the targets easily detectable. While, in most cases, such amplification and subsequent detection are typically done for one target nucleic molecule per reaction volume, it is of great interest to efficiently multiplex the assays in the same reaction volume and allow for multiple concurrent target amplification and detection in the same reaction chamber. Such an approach may not only better utilize the "precious" original DNA sample, but also significantly reduce any complexities associated with the fluidics and liquid-handling procedures for running multiple single-plex reactions.

SUMMARY

Recognized herein are various issues with currently available multiplexed PCR methods. For instance, while multiplexing a large number of target amplification reactions (e.g., multiplexed PCR) may be possible, it is not straightforward to detect multiple amplicons simultaneously. So far, multiplexed Q-PCR methods, defined as the processes by which one amplifies and detects a plurality of nucleic acid sequences simultaneously in a single reaction chamber, has been implemented for a small number of amplicons, generally less than ten. Accordingly, recognized herein is a need for methods and systems that enable multiplex nucleic acid amplification and real-time quantitative detection.

The present disclosure provides methods, devices and systems for amplifying a plurality of nucleic acid sequences and real-time monitoring the amplification processes and evaluating quantitatively the generated products, in a single reaction chamber.

An aspect of the present disclosure provides a method for assaying a presence or absence of at least one target nucleic acid molecule, comprising: (a) providing a reaction mixture comprising a nucleic acid sample suspected of containing the at least one template nucleic acid molecule, a primer pair and a polymerase, wherein the primer pair has sequence complementarity with the template nucleic acid molecule, and wherein the primer pair comprises a limiting primer and an excess primer; (b) subjecting the reaction mixture to a nucleic acid amplification reaction under conditions that yield the at least one target nucleic acid molecule as an amplification product of the template nucleic acid molecule; (c) bringing the reaction mixture in contact with a sensor array having (i) a substrate comprising a plurality of probes immobilized to a surface of the substrate at different individually addressable locations, wherein the probes are capable of capturing the target nucleic acid molecule and/or the limiting primer, and (ii) an array of detectors configured to detect at least one signal from the addressable locations, wherein the at least one signal is indicative of the presence or absence of the target nucleic acid molecule and/or the limiting primer; (d) using the array of detectors to detect the at least one signal from one or more the addressable locations at multiple time points during the nucleic acid amplification reaction; and (e) identifying the presence or absence of the target nucleic acid molecule and/or the limiting primer based on the at least one signal.

In some embodiments of aspects provided herein, the at least one signal is produced upon binding of the probes to the target nucleic acid molecule and/or the limiting primer. In some embodiments of aspects provided herein, the reaction mixture comprises a plurality of template nucleic acid molecules and the probes specifically bind to a plurality of target nucleic molecules as amplification products of the plurality of template nucleic acid molecules. In some embodiments of aspects provided herein, the reaction mixture comprises a plurality of limiting primers having different nucleic acid sequences, and the probes specifically bind to the plurality of the limiting primers. In some embodiments of aspects provided herein, the reaction mixture is provided in a reaction chamber configured to retain the reaction mixture and permit the probes to bind to the target nucleic acid molecule and/or the limiting primer. In some embodiments of aspects provided herein, the method further comprises correlating the detected at least one signal at multiple time points with an original concentration of the at least one template nucleic acid molecule by analyzing a binding rate of the probes with the target nucleic acid molecule or the limiting primer. In some embodiments of aspects provided herein, the probes are oligonucleotides. In some embodiments of aspects provided herein, the target nucleic acid molecule forms a hairpin loop when hybridized to an individual probe. In some embodiments of aspects provided herein, the sensor array comprises at least about 100 integrated sensors, at least about 500 integrated sensors, at least about 1,000 integrated sensors, at least about 2,000 integrated sensors, at least about 5,000 integrated sensors or at least about 10,000 integrated sensors. In some embodiments of aspects provided herein, the at least one signal is an optical signal that is indicative of an interaction between an energy acceptor and an energy donor. In some embodiments of aspects provided herein, the energy acceptor quenches optical activity of the energy donor. In some embodiments of aspects provided herein, the energy acceptor is coupled to the excess primer and/or the limiting primer. In some embodiments of aspects provided herein, the energy acceptor is coupled to the target nucleic acid molecule. In some embodiments of aspects provided herein, the energy acceptor is a quencher. In some embodiments of aspects provided herein, the energy donor is a fluorophore. In some embodiments of aspects provided herein, the at least one signal is an optical signal indicative of the activity of an optically-active species. In some embodiments of aspects provided herein, the optically-active species is an intercalator. In some embodiments of aspects provided herein, the optically-active species is a fluorophore. In some embodiments of aspects provided herein, the at least one signal is an electrical signal that is indicative of an interaction between an electrode and a redox label. In some embodiments of aspects provided herein, the redox label is coupled to the excess primer and/or the limiting primer. In some embodiments of aspects provided herein, the redox label is coupled to the target nucleic acid molecule. In some embodiments of aspects provided herein, (d) comprises measuring an increase in the at least one signal relative to background. In some embodiments of aspects provided herein, (d) comprises measuring a decrease in the at least one signal relative to background. In some embodiments of aspects provided herein, the sensor array comprises at least one optical detector that detects the at least one signal. In some embodiments of aspects provided herein, the optical detector comprises a complementary metal-oxide semiconductor (CMOS) device. In some embodiments of aspects provided herein, the sensor array comprises at least one electrical detector that detects the at least one signal. In some embodiments of aspects provided herein, the electrical detector comprises a complementary metal-oxide semiconductor (CMOS) device. In some embodiments of aspects provided herein, the probes are immobilized to the surface via a linker. In some embodiments of aspects provided herein, the linker comprises a species selected from the group consisting of an amino acid, a polypeptide, a nucleotide and an oligonucleotide. In some embodiments of aspects provided herein, the target nucleic acid molecule is detected at a sensitivity of at least about 90%, at least about 95%, at least about 98%, at least about 99%, at least about 99.9%, or at least about 99.99%. In some embodiments of aspects provided herein, the at least one signal is detected while the reaction mixture comprising the target nucleic acid molecule is in fluid contact with the sensor array. In some embodiments of aspects provided herein, the method further comprises detecting at least one control signal from the sensor array. In some embodiments of aspects provided herein, the at least one signal is detected in real-time.

Another aspect of the present disclosure provides a method for assaying a presence or absence of at least one target nucleic acid molecule, comprising: (a) providing a reaction mixture comprising a nucleic acid sample, a primer pair, a polymerase and a nucleotide labeled with a reporter molecule, wherein the nucleic acid sample is suspected of containing the at least one template nucleic acid molecule, and wherein the primer pair has sequence complementarity with the template nucleic acid molecule; (b) subjecting the reaction mixture to a nucleic acid amplification reaction under conditions that yield the at least one target nucleic acid molecule as an amplification product of the template nucleic acid molecule, which nucleic acid amplification reaction incorporates the nucleotide into the template nucleic acid molecule; (c) bringing the reaction mixture in contact with a sensor array comprising (i) a substrate comprising a plurality of probes immobilized to a surface of the substrate at different individually addressable locations, wherein the probes are capable of capturing the target nucleic acid molecule, and (ii) an array of detectors configured to detect at least one signal from the addressable locations upon interaction between the reporter molecule and at least one of the probes, wherein the at least one signal is indicative of the presence or absence of the target nucleic acid molecule; (d) using the array of detectors to detect the at least one signal from one or more the addressable locations at multiple time points during the nucleic acid amplification reaction; and (e) identifying the presence or absence of the target nucleic acid molecule based on the at least one signal.

In some embodiments of aspects provided herein, the at least one signal is produced upon binding of the probes to the target nucleic acid molecule comprising the reporter molecule. In some embodiments of aspects provided herein, the reaction mixture is provided in a reaction chamber configured to retain the reaction mixture and permit the probes to bind to the target nucleic acid molecule. In some embodiments of aspects provided herein, the nucleotide is deoxyribonucleotide triphosphate (dNTP). In some embodiments of aspects provided herein, the probes are oligonucleotides. In some embodiments of aspects provided herein, the target nucleic acid molecule forms a hairpin loop when hybridized to an individual probe. In some embodiments of aspects provided herein, the sensor array comprises at least about 100 integrated sensors, at least about 500 integrated sensors, at least about 1,000 integrated sensors, at least about 2,000 integrated sensors, at least about 5,000 integrated sensors or at least about 10,000 integrated sensors. In some embodiments of aspects provided herein, the reporter molecule is an energy acceptor. In some embodiments of aspects provided herein, the at least one signal is an optical signal that is indicative of an interaction between the energy acceptor and an energy donor. In some embodiments of aspects provided herein, the energy acceptor quenches optical activity of the energy donor. In some embodiments of aspects provided herein, the energy acceptor is a quencher. In some embodiments of aspects provided herein, the energy donor is a fluorophore. In some embodiments of aspects provided herein, the at least one signal is an optical signal indicative of the activity of an optically-active species. In some embodiments of aspects provided herein, the optically-active species is an intercalator. In some embodiments of aspects provided herein, the optically-active species is a fluorophore. In some embodiments of aspects provided herein, the reporter molecule is a redox label. In some embodiments of aspects provided herein, the at least one signal is an electrical signal that is indicative of an interaction between an electrode and the redox label. In some embodiments of aspects provided herein, (d) comprises measuring an increase in the at least one signal relative to background. In some embodiments of aspects provided herein, (d) comprises measuring a decrease in the at least one signal relative to background. In some embodiments of aspects provided herein, the sensor array comprises an optical detector that detects the at least one signal. In some embodiments of aspects provided herein, the optical detector comprises a complementary metal-oxide semiconductor (CMOS) device. In some embodiments of aspects provided herein, the sensor array comprises an electrical detector that detects the at least one signal. In some embodiments of aspects provided herein, the electrical detector comprises a complementary metal-oxide semiconductor (CMOS) device. In some embodiments of aspects provided herein, the probes are immobilized to the surface via a linker. In some embodiments of aspects provided herein, the linker comprises a species selected from the group consisting of an amino acid, a polypeptide, a nucleotide and an oligonucleotide. In some embodiments of aspects provided herein, the target nucleic acid molecule is detected as a sensitivity of at least about 90%, at least about 95%, at least about 98%, at least about 99%, at least about 99.9%, or at least about 99.99%. In some embodiments of aspects provided herein, the method further comprises detecting at least one control signal from the sensor array. In some embodiments of aspects provided herein, the at least one signal is detected in real-time. In some embodiments of aspects provided herein, the reporter molecule is a quencher. In some embodiments of aspects provided herein, the probes are labeled with fluorophores. In some embodiments of aspects provided herein, the reporter molecule is a fluorophore. In some embodiments of aspects provided herein, the probes are labeled with quenchers. In some embodiments of aspects provided herein, the at least one signal is indicative of an interaction between the quencher and a given one of the fluorophores.

Another aspect of the present disclosure provides a system for assaying a presence or absence of at least one target nucleic acid molecule, comprising: (a) a reaction chamber configured to (i) retain a reaction mixture comprising a nucleic acid sample suspected of containing the at least one template nucleic acid molecule, a primer pair that has sequence complementary to the template nucleic acid molecule, and a polymerase, wherein the primer pair comprises a limiting primer and an excess primer, and (ii) facilitate a nucleic acid amplification reaction on the reaction mixture to yield at least one target nucleic acid molecule as an amplification product of the template nucleic acid; (b) a sensor array comprising (i) a substrate comprising a plurality of probes immobilized to a surface of the substrate at different individually addressable locations, wherein the probes are capable of capturing the target nucleic acid molecule and/or the limiting primer; and (ii) an array of detectors configured to detect at least one signal from the addressable locations, wherein the at least one signal is indicative of a presence or absence of the target nucleic acid molecule and/or the limiting primer; and (c) a computer processor coupled to the sensor array and programmed to (i) subject the reaction mixture to the nucleic acid amplification reaction, and (ii) detect the at least one signal from one or more of the addressable locations at multiple time points during the nucleic acid amplification reaction. In some embodiments of aspects provided herein, the computer processor is programmed to detect the at least one signal while the reaction mixture comprising the target nucleic acid molecule is in fluid contact with the sensor array. In some embodiments of aspects provided herein, the computer processor is programmed to detect the at least one signal in real-time. In some embodiments of aspects provided herein, the sensor array comprises an optical detector that is capable of detecting the at least one signal. In some embodiments of aspects provided herein, the optical detector comprises a complementary metal-oxide semiconductor (CMOS) device. In some embodiments of aspects provided herein, the sensor array comprises an electrical detector that is capable of detecting the at least one signal. In some embodiments of aspects provided herein, the electrical detector comprises a complementary metal-oxide semiconductor (CMOS) device. In some embodiments of aspects provided herein, the sensor array comprises at least about 100 integrated sensors, at least about 500 integrated sensors, at least about 1000 integrated sensors, at least about 2000 integrated sensors, at least about 5000 integrated sensors or at least about 10,000 integrated sensors. In some embodiments of aspects provided herein, the computer processor is programmed to identify the presence or absence of the target nucleic acid molecule and/or the limiting primer based on the at least one signal.

Another aspect of the present disclosure provides a system for assaying a presence or absence of at least one target nucleic acid molecule, comprising: (a) a reaction chamber configured to (i) retain a reaction mixture comprising a nucleic acid sample suspected of containing the at least one template nucleic acid molecule, a primer pair that has sequence complementary to the template nucleic acid molecule, a polymerase, and a nucleotide labeled with a reporter molecule, and (ii) facilitate a nucleic acid amplification reaction on the reaction mixture to yield at least one target nucleic acid molecule as an amplification product of the template nucleic acid, which nucleic acid amplification reaction incorporates the nucleotide into the template nucleic acid molecule; (b) a sensor array comprising (i) a substrate comprising a plurality of probes immobilized to a surface of the substrate at different individually addressable locations, wherein the probes are capable of capturing the target nucleic acid molecule, and (ii) an array of detectors configured to detect at least one signal from the addressable locations upon interaction between the reporter molecule and at least one of the probes, wherein the at least one signal is indicative of the presence or absence of the target nucleic acid molecule; and (c) a computer processor coupled to the sensor array and programmed to (i) subject the reaction mixture to the nucleic acid amplification reaction, and (ii) detect the at least one signal from the addressable locations at multiple time points during the nucleic acid amplification reaction.

In some embodiments of aspects provided herein, the computer processor is programmed to detect the at least one signal while the reaction mixture comprising the target nucleic acid molecule is in fluid contact with the sensor array. In some embodiments of aspects provided herein, the computer processor is programmed to detect the at least one signal in real-time. In some embodiments of aspects provided herein, the sensor array comprises an optical detector that is capable of detecting the at least one signal. In some embodiments of aspects provided herein, the optical detector comprises a complementary metal-oxide semiconductor (CMOS) device. In some embodiments of aspects provided herein, the sensor array comprises an electrical detector that is capable of detecting the at least one signal. In some embodiments of aspects provided herein, the electrical detector comprises a complementary metal-oxide semiconductor (CMOS) device. In some embodiments of aspects provided herein, the sensor array comprises at least about 100 integrated sensors, at least about 500 integrated sensors, at least about 1000 integrated sensors, at least about 2000 integrated sensors, at least about 5000 integrated sensors or at least about 10,000 integrated sensors. In some embodiments of aspects provided herein, the computer processor is programmed to identify the presence or absence of the target nucleic acid molecule based on the at least one signal.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
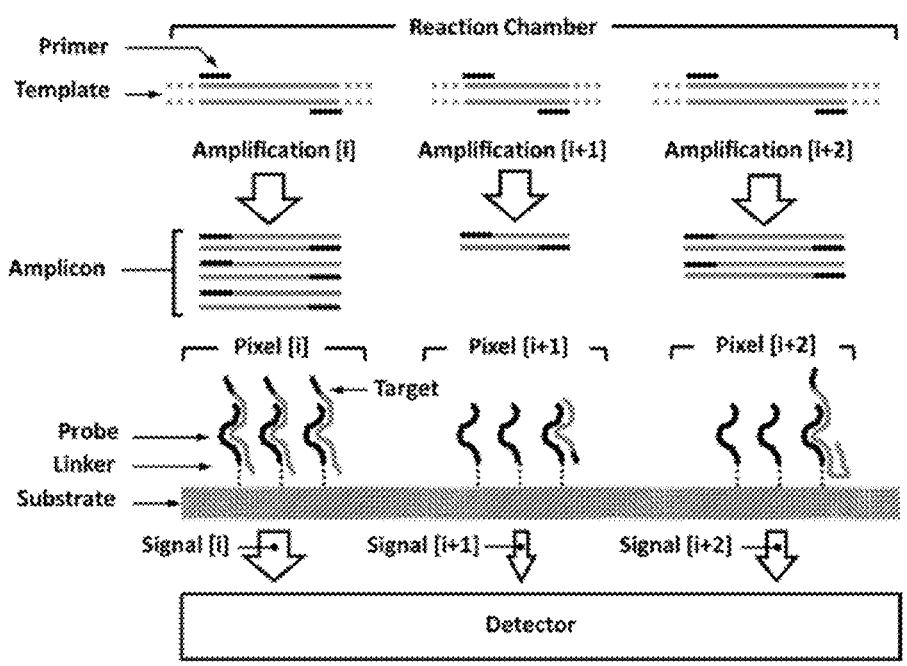
FIG. 1 schematically illustrates an example multiplex amplification and detection system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "quantitative-PCR" or "Q-PCR," as used herein generally refers to a polymerase chain reaction (PCR) process that can be used for the qualitative and quantitative determination of nucleic acid sequences. In some cases, Q-PCR is synonymous with real-time PCR. Q-PCR can involve the measurement of the amount of amplification product (or amplicon) as a function of amplification cycle, and use such information to determine the amount of the nucleic acid sequence corresponding to the amplicon that was present in the original sample.

The term "probe" as used herein generally refers to a molecular species or other marker that can bind to a specific target nucleic acid sequence. A probe can be any type of molecule or particle. Probes can comprise molecules and can be bound to the substrate or other solid surface, directly or via a linker molecule.

The term "detector" as used herein generally refers to a device, generally including optical and/or electronic components that can detect signals.

The term "mutation" as used herein generally refers to genetic mutations or sequence variations such as a point mutation, a single nucleotide polymorphism (SNP), an insertion, a deletion, a substitution, a transposition, a translocation, a copy number variation, or another genetic mutation, alteration or sequence variation.

The term "about" or "nearly" as used herein generally refers to within +/−15%, 10%, 9%, 8%, 7%, 6%, 5%, 4%, 3%, 2%, or 1% of the designated amount.

The term "label" as used herein refers to a specific molecular structure that can be attached to a target molecule, to make the target molecule distinguishable and traceable by providing a unique characteristic not intrinsic to the target molecule.

The term "limiting," as used herein in the context of a chemical or biological reaction, generally refers to a species that is in a limiting amount (e.g., stoichiometrically limiting) in a given reaction volume such that upon completion of the chemical or biological reaction (e.g., PCR), the species may not be present in the reaction volume.

The term "excess," as used herein in the context of a chemical or biological reaction, generally refers to a species that is in an excess amount (e.g., stoichiometrically limiting) in a given reaction volume such that upon completion of the chemical or biological reaction (e.g., PCR), the species may be present in the reaction volume.

The term "nucleotide," as used herein, generally refers a molecule that can serve as the monomer, or subunit, of a nucleic acid, such as deoxyribonucleic acid (DNA) or ribonucleic acid RNA). A nucleotide can be a deoxynucleotide triphosphate (dNTP) or an analog thereof, e.g., a molecule having a plurality of phosphates in a phosphate chain, such as 2, 3, 4, 5, 6, 7, 8, 9, or 10 phosphates. A nucleotide can generally include adenosine (A), cytosine (C), guanine (G), thymine (T) and uracil (U), or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. A nucleotide may be labeled or unlabeled. A labeled nucleotide may yield a detectable signal, such as an optical, electrostatic or electrochemical signal.

A Q-PCR process can be described in the following non-limiting example. A PCR reaction is carried out with a pair of primers designed to amplify a given nucleic acid sequence in a sample. The appropriate enzymes and nucleotides, such as deoxynucleotide triphosphates (dNTPs), are added to the reaction, and the reaction is subjected to a number of amplification cycles. The amount of amplicon generated from each cycle is detected, but in the early cycles, the amount of amplicon can be below the detection threshold. The amplification may be occurring in two phases, an exponential phase, followed by a non-exponential plateau phase. During the exponential phase, the amount of PCR product approximately doubles in each cycle. As the reaction proceeds, however, reaction components are consumed, and ultimately one or more of the components becomes limiting. At this point, the reaction slows and enters the plateau phase. Initially, the amount of amplicon remains at or below background levels, and increases are not detectable, even though amplicon product accumulates exponentially. Eventually, enough amplified product accumulates to yield a detectable signal. The cycle number at which this occurs is called the threshold cycle, or $C_t$. Since the $C_t$ value is measured in the exponential phase when reagents are not limited, Q-PCR can be used to reliably and accurately calculate the initial amount of template present in the reaction. The $C_t$ of a reaction may be determined mainly by the amount of nucleic acid sequence corresponding to amplicon present at the start of the amplification reaction. If a large amount of template is present at the start of the reaction, relatively few amplification cycles may be required to accumulate enough products to give a signal above background. Thus, the reaction may have a low, or early, $C_t$. In contrast, if a small amount of template is present at the start of the reaction, more amplification cycles may be required for the fluorescent signal to rise above background. Thus, the reaction may have a high, or late, $C_t$. Methods and systems provided herein allow for the measurement of the accumulation of multiple amplicons in a single fluid in a single amplification reaction, and thus the determination of the amount of multiple nucleic acid sequences in the same sample with the methodology of Q-PCR described above.

As used herein in, the term "real-time" generally refers to measuring the status of a reaction while it is occurring, either in the transient phase or in biochemical equilibrium. Real-time measurements are performed contemporaneously with the monitored, measured, or observed ongoing events, as opposed to measurements taken after a reaction is fixed. Thus, a "real time" assay or measurement generally contains not only the measured and quantitated result, such as fluorescence, but expresses this at various time points, that is, in nanoseconds, microseconds, milliseconds, seconds, minutes, hours, etc. "Real-time" may include detection of the kinetic production of signal, comprising taking a plurality of readings in order to characterize the signal over a period of time. For example, a real-time measurement can comprise the determination of the rate of increase or decrease in the amount of an analyte. While the measurement of signal in real-time can be useful for determining rate by measuring a change in the signal, in some cases the measurement of no change in signal can also be useful. For example, the lack of change of a signal over time can be an indication that a reaction (e.g., binding, hybridization) has reached a steady-state.

As used herein, the terms "polynucleotide", "oligonucleotide", "nucleotide", "nucleic acid" and "nucleic acid molecule" generally refer to a polymeric form of nucleotides (polynucleotides) of various lengths (e.g., 20 bases to 5000 kilo-bases), either ribonucleotides (RNA) or deoxyribonucleotides (DNA). This term may refer only to the primary structure of the molecule. Thus, the term may include triple-, double- and single-stranded DNA, as well as triple-, double- and single-stranded RNA. It may also include modifications, such as by methylation and/or by capping, and unmodified forms of the polynucleotide.

Nucleic acids can comprise phosphodiester bonds (i.e. natural nucleic acids). Nucleic acids can comprise nucleic acid analogs that may have alternate backbones, comprising, for example, phosphoramide (see, e.g., Beaucage et al., Tetrahedron 49(10):1925 (1993) and U.S. Pat. No. 5,644,048), phosphorodithioate (see, e.g., Briu et al., J. Am. Chem. Soc. 11 1:2321 (1989), O-methylphosphoroamidite linkages (see, e.g., Eckstein, Oligonucleotides and Analogues: A Practical Approach, Oxford University Press), and peptide nucleic acid (PNA) backbones and linkages (see, e.g., Carlsson et al., Nature 380:207 (1996)). Nucleic acids can comprise other analog nucleic acids including those with positive backbones (see, e.g., Denpcy et al., Proc. Natl. Acad. Sci. USA 92:6097 (1995); non-ionic backbones (see, e.g., U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, (see, e.g., U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook). Nucleic acids can comprise one or more carbocyclic sugars (see, e.g., Jenkins et al., Chem. Soc. Rev. (1995) pp 169-176). These modifications of the ribose-phosphate backbone can facilitate the addition of labels, or increase the stability and half-life of such molecules in physiological environments.

As used herein, the term "amplicon" generally refers to a molecular species that is generated from the amplification of a nucleotide sequence, such as through PCR. An amplicon may be a polynucleotide such as RNA or DNA or mixtures thereof, in which the sequence of nucleotides in the amplicon may correlate with the sequence of the nucleotide sequence from which it was generated (i.e. either corresponding to or complimentary to the sequence). The amplicon can be either single stranded or double stranded. In some cases, the amplicon may be generated by using one or more primers that is incorporated into the amplicon. In some cases, the amplicon may be generated in a polymerase chain reaction or PCR amplification, wherein two primers may be used to produce either a pair of complementary single stranded amplicons or a double-stranded amplicon.

As used herein, the term "probe" generally refers to a molecular species that is a marker that can bind to a nucleic acid sequence. A probe can be any type of molecules or particles. Probes can comprise molecules and can be bound to a substrate or a surface, directly or via a linker molecule.

As used herein, the singular forms "a", "an", and "the" include plural references unless the context clearly dictates otherwise.

Overview

Quantification of amplicons during amplification processes, to enable Q-PCR, may be done based on measuring the light intensity or spectral pattern (e.g., frequency, frequency distribution or intensity distribution) emanating from fluorescent reporter molecules that have signal intensity associated with the generated PCR products. The measured light intensity in these processes may be used as an indication of the actual number of the amplified sequences and the amplification process. Some of the used methods, in single-plex PCR or other amplification processes, may comprise intercalator fluorophore dyes that can bind to double-stranded DNA (dsDNA) such as SYBR Green or short modified DNA sequences in the form of hybridization or TaqMan probes.

Attempts at creating multiplex Q-PCR methods have been plagued by practical issues of simultaneously detecting different nucleic acid sequences in a single sample. A possible approach is to associate different reporter molecules (e.g., fluorescent dyes) to individual amplicons during the PCR reaction which may enable parallel detection of individual reporters by different "colors". While such approach, in theory, may offer parallelism, is limited by (i) the number of different reporter molecules available; and (ii) the availability of imagers and detectors capable of differentiating different signals. Current Q-PCR systems may be able to detect up to ten amplicons by using up to ten different fluorescent reporters. Another possible approach to offer multiplexing capability is to divide the biological sample of interest and physically place it, using fluidic systems, into separate, single and isolated amplification chambers. While this approach may effectively create multiplex Q-PCR by performing multiple single-plex (i.e., one amplicon per chamber) Q-PCR reactions, it may be suboptimal, since it may reduce the number of nucleic acid target sequences in each chamber which may create stochastic anomalies (Poisson noise) in the acquired data when the original sample has a small concentration. Further, it requires complex fluidic handling procedures.

Highly-multiplexed detection of DNA sequences in a sample may be done through adopting analytical platforms such as DNA microarrays or next generation DNA sequencers, but not Q-PCR or equivalent. Microarrays, in particular, are massively-parallel affinity-based biosensor where nucleic acid targets are captured selectively from the same sample at different addressable coordinates (e.g., pixels) on a solid surface. Each addressable coordinate can have a unique capturing DNA or RNA probe, complementary to a target specific sequence to be detected in the sample. While microarrays may offer high multiplexing capability, they are semi-quantitative and are inferior in terms of limit-of-detection (LOD) and detection dynamic range (DDR), due to their end-point detection nature (i.e., no real-time detection) and the fact that they lack any target amplification.

The present disclosure provides methods, devices and systems by which one can achieve the multiplexing capabilities of microarrays while having the LOD and DDR of Q-PCR methods. The methods and systems provided herein may be used to create unique nucleic acid detection platform and may find useful in a wide context of applications, such as molecular diagnostics, DNA forensics, and pathogen genotyping, etc.

The methods, devices and systems described herein may be used for simultaneously performing a plurality of reactions (e.g., a biochemical reaction, a chemical reaction) and real-time monitoring the progress of the reactions via, for example, detecting and/or determining the presence or absence, amount, quantity, concentration, activity and/or binding characteristics of one or more target substances (e.g., analytes, reagents and/or products including primers, amplicons, nucleic acid sequences) in a single reaction chamber. The amount, quantity, concentration, activity and/or binding characteristics of target substances may be monitored and/or determined by detecting signals produced upon the occurrence of binding between the target substances and the probes contained within multiple independently addressable locations. With provided methods and systems of the present disclosure, the presence or absence of the target substances may be determined with high sensitivity and/or specificity. For example, the presence or absence of a target analyte may be determined or detected at a sensitivity of at least about 50%, 60%, 70%, 80%, 85%, 90%, 91%, 92%, 93%, 94%, 95%, 96%, 97%, 98%, 99%, 99.9%, 99.99%, 99.999%, or 99.9999%. Similarly, the sensitivity of the methods provided herein may be at least about 50%, 60%, 70%, 80%, 85%, 90%, 91%, 92%, 93%, 94%, 95%, 96%, 97%, 98%, 99%, 99.9%, 99.99%, 99.999%, or 99.9999%.

The systems and methods provided herein may comprise a chip which further comprises an integrated sensor array. The sensor array may comprise a substrate and a plurality of probes (e.g., an array of probes) that attached or immobilized to a surface of the substrate. The sensor array may also comprise a single or a plurality of integrated sensors that may be capable of detecting or capturing a signal produced once the probes bind to one or more analytes (e.g., a target nucleic acid molecule, a template nucleic acid molecule, a primer, an amplicon, a polymerase) in a reaction mixture. As provided herein, any number of sensors may be used. In some cases, a small number of sensors may be included. In some cases, a large number of sensors may be used. In some cases, a system may comprise less than or equal to about 1,000,000, 750,000, 500,000, 250,000, 100,000, 75,000, 50,000, 25,000, 10,000, 7,500, 5,000, 2,500, 1,000, 900, 800, 700, 600, 500, 400, 300, 200, 100, 80, 60, 40, 20, 5, or 1 sensor. In some cases, a system may comprise at least about 1, 10, 30, 50, 70, 90, 100, 300, 500, 700, 900, 1,100, 1,500, 2,000, 4,000, 6,000, 8,000, 10,000, 20,000, 30,000, 40,000, 50,000, 60,000, 70,000, 80,000, 90,000, 100,000, 250,000, or 500,000 sensors. The sensors may be integrated sensors. The sensors can be individually (or independently) addressable. In some cases, the number of sensors comprised in a system may be between any of the two values described herein, for example, about 12,500.

FIG. 1 shows an example multiplexed amplification and detection system of the present disclosure. As FIG. 1 illustrates, the system comprises a reaction chamber having a number of reagents (e.g., primer, template nucleic acid molecule) required for a nucleic acid amplification reaction, a probe array having three independently addressable locations (i.e., pixel [i], [i+1] and [i+2]) and a detector capable of real-time detecting signals produced in each pixels. The probes are attached to the substrate of the probe array via a linker. For each addressable location, a different type of probe that can specifically bind to a single type of target substance (i.e., amplicons [i], [i+1] and [i+2] produced within each location) is included. Upon binding of the amplicon to the probe, signals reflective of the binding events on each pixel (i.e., signal [i], [i+1] and [i+2]) may be generated and captured by the detector. By analyzing the detected signals, progress of amplification reactions within each location may be determined in parallel.

The methods, devices and systems provided herein may utilize real-time microarray systems. Examples of such systems may be found in, for example, U.S. Patent Pub. Nos. 2010/0122904, 2013/0345065, 2014/0001341, 2014/0318958, 2014/0011710, 2012/0168306, 2013/0225441, 2012/0077692, 2007/0099198, 2008/0081769, 2008/0176757 and 2008/0039339, and U.S. Pat. Nos. 8,637,436, 8,048,626, and 8,518,329, each of which is entirely incorporated herein by reference.

Systems of the present disclosure may include at least one reaction chamber, a probe array and a detection system. The reaction chamber may be configured to perform functions of one or more reactions (e.g., nucleic acid amplification processes or PCR). The nucleic acid amplification processes may include biochemical processes that can specifically increase the copy number of specific nucleotide sequences and label the generated products (i.e., amplicons) with reporter molecules (i.e., "labels") in a single reaction chamber. The reaction chamber can include an aqueous environment in which a plurality of free-moving analytes (e.g., nucleic acid sequences to be detected) or reagents (e.g., primers, probes, chemical surface modifiers and polymerase) is present. The probe array may comprise a plurality of nucleic acid probes at independently addressable locations on a solid surface. Each addressable location (e.g., "pixel") may include a plurality of identical nucleic acid sequences (or "probes") that can specifically hybridize or bind to a specific amplicon and/or other nucleic sequences in the reaction chamber. The probes and/or the analytes may be labeled with one or more reporter molecules (e.g., energy acceptors, energy donors). In some examples, the probes can be labeled with energy acceptors. The energy acceptors can be quenchers. In such a case, the analytes (such as dNTPs, primers) can be labeled with energy donors. The energy donors can be fluorophores. As an alternative, the probes can be labeled with energy donors. The energy donors can be fluorophores. In such a case, the analytes can be labeled with energy acceptors. The energy acceptors can be quenchers.

The detection system may comprise one or more detectors. The detector can real-time measure the generated signal in parallel at each addressable location that is indicative of the progress of the reaction. For example, for PCR reaction, the detected signal may be reflective of the presence and activity of reporter molecules in its vicinity, as the reaction progresses and the probe/target sequence interactions occur.

Reaction Chamber

The methods, devices and systems of the present disclosure may comprise a single reaction chamber or a plurality of reaction chambers. The reaction chamber may comprise a plurality of sub-reaction chambers that are in fluid communication with each other. The reaction chamber may be separated from the probe array and detection system. The reaction chamber may be integrated with the probe array and/or the detection system. The reaction chamber may comprise at least one sample inlet. The reaction chamber may further in electric communication with a temperature control module is configured to alter, control and/or maintain the temperature in the reaction chamber. The reaction chamber may be configured to retain a reaction mixture and facilitate an amplification reaction of one or more target analytes in the reaction mixture. The reaction mixture may comprise analytes such as, template nucleic acid molecule to be amplified, primer pairs, limiting primers, excess primers, polymerases, nucleotides, solvent, or any other reagents that may be required for a reaction. Any of the analytes in the reaction mixture may be labeled by one or more reporter molecules. Binding of the probes and analytes that comprise the reporter molecules may produce a signal that can be captured or detected by an integrated sensor. Such signal may be indicative of a presence or absence of one or more analytes in the reaction mixture, or the process of the reaction. The signals may be detected at a single time point or multiple time points. The signals may also be monitored in real-time. While detecting the signals from the reaction mixture, the reaction mixture may or may not be in contact with the sensor. In some cases, detecting signals comprises measuring or determining an increase of a signal relative to background. In some cases, detecting signals comprises measuring or observing a decrease of a signal relative to background. Background signal may refer to a signal detected or obtained prior the occurrence of the binding event. The detecting may also comprise measuring or detecting at least one control signal. The control signal may be generated upon binding of the probes with a control sample having a known sequence.

A reaction chamber can comprise a closed reservoir. The reaction chamber can have a volume from about 100 mL to about 1 nL. In some cases, the reaction chamber volume is from about 100 µL to about 1 µL.

A reaction chamber can contain a solution (e.g., an aqueous solution). The aqueous solution within the reaction chamber can comprise a buffered saline-based solution, such as an aqueous solution comprising a mixture of a weak acid and its conjugate base, or vice versa. The solution can comprise a plurality of target substances (e.g., nucleic acid sequences). The term "nucleic acid sequence" or "nucleotide sequence" as used in this context refers to nucleic acid molecules with a given sequence of nucleotides, of which it is desired to know the presence and/or amount. The nucleotide sequence can comprise RNA or DNA, or a sequence derived from RNA or DNA. Examples of nucleotide sequences are sequences corresponding to natural or synthetic RNA or DNA including genomic DNA and messenger RNA. The length of the sequence can be any length that can be amplified into amplicons, for example up to about 5, 10, 20, 50, 100, 200, 300, 400, 500, 600, 700, 800, 1,000, 1,200, 1,500, 2,000, 5,000, 10,000 or more than 10,000 nucleotides in length.

In some cases, target analytes may include reporter molecules (e.g., labels). The reporter molecules can comprise molecular structures that, once attached to a nucleic acid sequence, provide a distinct characteristic that is not inherent to those nucleic acid molecules. Examples are labels that create unique optical characteristics.

Probe Arrays

As described herein, the terms "array" and "microarray" can be used interchangeably. A probe array may comprise a surface having a plurality of probes attached thereto, where the array can be used for the real-time measurement and/or detection of the presence, amount, concentration, and/or binding characteristics of multiple analytes (e.g., amplicons). In some cases, one or more probes may be located on a plurality of discrete, isolated and independently addressable locations.

The substrate may be solid or semi-solid. The substrate may be biological, non-biological, organic, inorganic, or a combination of any of these, existing as a form of particles, strands, precipitates, gels, sheets, tubing, spheres, containers, capillaries, pads, slices, films, plates, slides, semiconductor integrated chips, etc. The substrate may take on any surface configurations (e.g., flat). For example, the substrate may contain raised or depressed regions on which synthesis or deposition may take place. In some cases, the substrate may be chosen to provide appropriate light-absorbing characteristics. For example, the substrate may be a polymerized Langmuir Blodgett film, functionalized glass, Si, Ge, GaAs, Gap, $SiO_2$, $SiN_4$, modified silicon, or any one of a variety of gels or polymers such as (poly)tetrafluoroethylene, (poly)vinylidenedifluoride, polystyrene, polycarbonate, or combinations thereof.

The substrate may be a homogeneous solid and/or unmoving mass with dimensions much larger than the probes. In some cases, the probes may be confined and/or immobilized within a certain distance of the substrate. The mass of the substrate may be at least 100 times larger than that of the probe. The surface of the substrate may be planar or non-planar. Examples of non-planar substrates may include spherical magnetic beads, spherical glass beads, and solid metal and/or semiconductor and/or dielectric particles. In cases where the substrate comprises a planar surface, the roughness of the surface may vary. In some cases, the roughness of the substrate surface may be less than or equal to about 1000 nanometers (nm), 750 nm, 500 nm, 250 nm, 100 nm, 90 nm, 80 nm, 70 nm, 60 nm, 50 nm, 40 nm, 30 nm, 20 nm, 10 nm, 5 nm, 1 nm, 0.75 nm, 0.5 nm, 0.25 nm, 0.1 nm, 0.05 nm, 0.25 nm, 0.01 nm, 0.005 nm, or 0.001 nm. In some cases, the surface of the substrate may have a roughness greater than or equal to about 0.0001 nm, 0.0005 nm, 0.001 nm, 0.005 nm, 0.01 nm, 0.05 nm, 0.1 nm, 0.5 nm, 1 nm, 5 nm, 10 nm, 20 nm, 30 nm, 40 nm, 50 nm, 60 nm, 70 nm, 80 nm, 90 nm, 100 nm, 200 nm, 300 nm, 400 nm, or 500 nm. In some cases, the roughness of the substrate surface may be between nay of the two values described herein, for example, about 75 nm.

The substrate can be optically clear, allowing transmission of the light through the substrate, and excitation and/or detection to occur as the light passing through the substrate. The substrate can also be translucent or opaque. In some cases, the substrate can be reflective, allowing for light to pass through the surface layer containing probes and reflect back to a detector.

In some cases, the array may be incorporated into the reaction chamber in which the amplification reaction takes place. The array may be part of the wall or base of the chamber. The array may mate with other components, forming a seal, and creating a reaction chamber for carrying out the amplification reaction.

The substrate can be made of various materials. Non-limiting examples of materials may include silica, silicon, plastic, glass, metal, metal-alloy, nanopore, polymer, and nylon. Surface of the substrate can be treated with a layer of chemicals prior to attaching probes to enhance the binding and/or to inhibit non-specific binding during use. For example, the substrate may comprise glass slide, which can be coated with self-assembled monolayer (SAM) coatings, such as coatings of as aminoalkyl silanes, or of polymeric materials, such as acrylamide and proteins. A variety of can be used, for example, 3D-Link® (Surmodics), EZ-Rays® (Mosaic Technologies), Fastslides® (Schleicher and Schuell), Superaldehyde®, and Superamine® (CEL Technologies).

Probes may be associated with, attached to, or bonded to the substrate. The association, attachment or bonding of the probes may be reversible or irreversible. The association, attachment or bonding of the probes may be chemical, biological, or biochemical. In some cases, the probes may be associated with, attached to or bonded with the substrate via a linker. The linker may be any type of molecules (chemical or biological) that is capable of linking the probes with the substrate. In some cases, the linker can be a chemical bond. For example, the probes can be attached covalently to the surface of the substrate.

A number of different chemical surface modifiers can be added to substrates to attach the probes to the substrates. Examples of chemical surface modifiers may include, but not limited to, N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, phosphines, and combinations thereof. In one cases, substrate surfaces reactive towards amines may be utilized. Examples of such surfaces may include NHS-esters, aldehyde, epoxide, acyl halide, and thio-ester. Molecules (e.g., proteins, peptides, glycopeptides) with free amine groups may react with such surfaces to form covalent bond with the surfaces. Nucleic acid probes with internal or terminal amine groups can also be synthesized, (e.g., from IDT or Operon) and bound (e.g., covalently or non-covalently) to surfaces using similar chemistries.

Surface of the substrate may or may not be reactive towards amines. In cases where an amine-reactive substrate is needed, the substrate surface may be converted into amine-reactive substrates with coatings. Non-limiting examples of coatings may include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), BSA coatings (which can be reacted with bis-NHS cross-linkers, maleimide-NHS cross-linkers, etc.), or combinations thereof. Alternatively, in some cases, the probes, rather than the substrate, can be reacted with specific chemical modifiers to make them reactive to the respective surfaces.

A number of multi-functional cross-linking agents can be used to convert the chemical reactivity of one type of surface to another. The agents can be homo-functional or hetero-functional. The agents can be bi-functional, tri-functional, or tetra-functional, for example, a bi-functional cross-linking agent X—Y—Z, with X and Z being two reactive groups, and Y being a connecting linker. Further, if X and Z are the same group, such as NHS-esters, the resulting cross-linker, NHS—Y—NHS, is a homo-bi-functional cross-linker and may connect an amine surface with an amine-group containing molecule. If X is NHS-ester and Z is a maleimide group, the resulting cross-linker, NHS—Y-maleimide, is a hetero-bi-functional cross-linker and may link an amine surface (or a thiol surface) with a thio-group (or amino-group) containing probe. Examples of such agents may include, but not limited to NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), and combinations thereof. Such cross-linkers can be reacted with the surface or with the probes or with both, in order to conjugate a probe to a surface.

Additionally or alternatively, a substrate may include thiol reactive surfaces such as acrylate, maleimide, acyl halide and thio-ester surfaces. Such surfaces can covalently link proteins, peptides, glycopeptides, etc., via a thiol group. Nucleic acid probes containing pendant thiol-groups can also be easily synthesized.

Various alternative surface modification techniques may be utilized in the present disclosure, for example, photo-crosslinkable surfaces and thermally cross-linkable surfaces. Examples of such techniques may include Mosiac Technologies (Waltham, Mass.), Exigon™ (Vedbaek, Denmark), Schleicher and Schuell (Keene, N.H.), Surmodics™ (St. Paul, Minn.), Xenopore™ (Hawthorne, N.J.), Pamgene (Netherlands), Eppendorf (Germany), Prolinx (Bothell, Wash.), Spectral Genomics (Houston, Tex.), and Combimatrix™ (Bothell, Wash.).

Various materials may be used to fabricate the surface of the substrate. Exemplary materials may include glass, metal (e.g., gold, silicon, copper, titanium, and aluminum), metal oxides (e.g., titanium oxide, iron oxide), silicon-based material (e.g., silicon, silica), plastics, polymer (e.g., polystyrene, polyethylene, polypropylene), zeolites, and combinations thereof. In some cases, the devices and systems provided herein may comprise LED (Light Emitting Diode) and OLED (Organic Light Emitting Diode) surfaces. An array of LEDs or OLEDs can be used at the base of a probe array. Such systems may be advantageous since they provide easy optoelectronic methods of result readout. In some cases, the results can be read-out using a naked eye.

Probes can be deposited onto the substrates, e.g., onto a modified surface, using either contact-mode printing methods using solid pins, quill-pins, ink jet systems, ring-and-pin systems, etc. (see, e.g., U.S. Pat. Nos. 6,083,763 and 6,110, 426) or non-contact printing methods (using piezoelectric, bubble-jet, syringe, electro-kinetic, mechanical, or acoustic methods. Example devices that may be used to deposit and distribute probes onto substrate surfaces may include, e.g., devices produced by Packard Instruments or devices for depositing, e.g., spotting, probes onto substrates include solid pins or quill pins (Telechem/Biorobotics).

As described elsewhere herein, the plurality of probes may be located on multiple independently addressable locations (or regions) on the substrate. The addressable locations may be distributed evenly or unevenly across the substrate. In some cases, each of the addressable locations may contain at least one probe. In some cases, only a certain percentage of the addressable locations may contain probes. The addressable locations without probes may act as control spots in order to increase the quality of the measurement, for example, by using binding to the spot to estimate and correct for non-specific binding. In some cases, less than or equal to about 1, 5, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 25,000, 50,000, 75,000, 100,000, 250,000, 500,000, 750,000, or 1,000,000 addressable regions may contain probes. In some cases, greater than or equal to about 1, 10, 25, 50, 75, 100, 200, 400, 600, 800, 1,000, 2,000, 3,000, 4,000, 5,000, 6,000, 7,000, 8,000, 9,000, 10,000, 25,000, 50,000, 75,000, 100, 000, 250,000, 500,000, 750,000, or 1,000,000 addressable regions may contain probes. In some cases, the number of addressable locations that contain probes may be between any of the two values described herein, for example, about 30,000.

Number of probes comprised in each occupied addressable location (i.e., addressable location having at least one probe) may vary. In some cases, each occupied addressable location may contain the same number of probes. In some cases, each occupied addressable location may contain a different number of probes. In some cases, a certain percentage of the occupied addressable locations may comprise the same or a different number of probes, for example, about 5%, 10%, 20%, 30%, 40%, 50%, 60%, 70%, 80%, 90%, or 100% of the occupied addressable locations may contain the same or a different number of probes.

In cases where more than one type of probes is utilized, probe type contained in the occupied addressable locations may vary. In some cases, it may be preferred to have different types of probes contained in each of the occupied addressable locations. In some cases, it may be necessary to have a certain percentage of the occupied addressable locations that contain the same or a different type of probes, for example, about 1%, 5%, 10%, 20%, 30%, 40%, 50%, 60%, 70%, 80%, 90%, or 100% of the occupied addressable locations may contain the same or a different type of probes.

In some cases, it may be useful to have redundant addressable locations which have identical probes to another addressable location. Probe arrays with such addressable location combinations can be less susceptible to fabrication non-idealities and measurement errors.

The shape of the cross-section of each addressable location may vary, for example, square, round, oval, triangle, rectangle, polygonal or any other arbitrary shape.

The cross-sectional dimension of the addressable locations may vary. In some cases, the addressable locations may have a large cross-sectional dimension. In some cases, addressable locations with small cross-sectional dimension may be used. In some cases, each side of the cross-section of the addressable location may be less than or equal to about 1 millimeter (mm), 750 micron ($\mu$m), 500 $\mu$m, 250 $\mu$m, 100 $\mu$m, 50 $\mu$m, 25 $\mu$m, 10 $\mu$m, 1 $\mu$m, 750 nm, 500 nm, 250 nm, 100 nm, 75 nm, 50 nm, 25 nm, 10 nm, 5 nm, 1 nm, 0.5 nm, 0.1 nm, 0.05 nm, or 0.01 nm. In some cases, each side of the cross-section of the addressable location may be greater than or equal to about 0.001 nm, 0.005 nm, 0.0075 nm, 0.1 nm, 0.5 nm, 0.75 nm, 1 nm, 25 nm, 50 nm, 75 nm, 100 nm, 250 nm, 500 nm, 750 nm, 1 micron ($\mu$m), 10 $\mu$m, 20 $\mu$m, 50 $\mu$m, 75 $\mu$m, 100 $\mu$m, 250 $\mu$m, 500 $\mu$m, 750 $\mu$m, or 1 mm. In some cases, each side of the addressable location may have a dimension falling between any of the values described herein, for example, about 5 $\mu$m. As will be appreciated, each addressable location may or may not have the same cross-sectional dimension.

The probes in the present disclosure may or may not be labeled with a reporter molecule. The reporter molecule can be bound to the probe by various methods, such as hybridization. In some cases, specific labels can be attached to the probes within the addressable locations, in addition to the labels that are incorporated. In such systems, captured targets can result in two labels coming into intimate proximity with each other in the location. This interaction between labels can create unique detectable signals. For example, when the labels on the target and probe, respectively, are fluorescent donor and acceptor moieties that can participate in a fluorescent resonance energy transfer (FRET) phenomenon, FRET signals can be detected. However, in some cases the interaction is not FRET.

In some cases, the analyte (e.g., dNTPs) in the reaction mixture is labeled with a first type of reporter molecule and the surface of an array is labeled with a second type of report molecule, wherein the second type of report molecule is not linked to or associated with the probe (e.g., a surface bound reporter molecule). Binding of the analyte to the probe will bring two types of reporter molecules into close proximity and therefore results in a change of the signals (e.g., an increase or a decrease) detected from the surface of the array or the reaction mixture. Such signal change may then be used to, e.g., determine a presence or absence of the analyte. For example, the analyte and the array surface may be labeled with a quencher and a light-emitting reporter molecule (e.g., a fluorophore), respectively, and the fluorescence from the fluorophore on the surface is quenched (or reduced) upon binding of the analyte to the probe. While the quencher does not emit a light signal, there is no signal from the reaction mixture (or solution) interfering with the signal from the array, which then substantially diminishes the noise at the array surface and enables the real-time measurement of signals at the array surface. Alternatively, in some examples, quenching moieties (e.g., quenchers) are attached to the array surface and the analyte is tagged with a light-emitting reporter (e.g., a fluorescent label). Upon binding of the analyte to the surface-bound probe, a decrease of fluorescent signals from the reaction mixture can be detected.

Detection System

Also provided herein is a detection system having at least one detector that is configured to capture, detect and/or monitor signals from the array. Various signals may be produced, such as optical, electrical, electrochemical, magnetic, mechanical, acoustic, or electromagnetic signals. The signals may be correlated with the presence, amount, concentration, and/or binding characteristics of one or more species (e.g., primers, amplicons, nucleic acid sequences, reporter molecules, polymerases, dNTPs, or any other analytes and reagents). The signals can be reflective or indicative of the progress of one or more reactions (e.g., PCR amplification). The signals can be detected at a single time point or multiple time points, or in real-time.

The detection system may comprise a single detector or a plurality of detectors (e.g., an array of detector). The detector(s) may be fixed or movable. The detectors may scan the probe array such that a given detector detects signals from different addressable locations of the array during the reaction process. In cases where a plurality of detectors is comprised in the detection system, the number of detectors may correspond to the same independently addressable locations contained in a probe array. For example, a fixed detector array may be used, wherein each of the detectors may correspond to an individual addressable location of a probe array. Any number of detectors may be utilized in the detection system as provided herein, for example, about 1, 10, 50, 100, 250, 500, 1,000, 2,500, 5,000, 7,500, 10,000, 25,000, 50,000, 75,000, 100,000, 250,000, 500,000, 750,000, or 1,000,000 detectors. The detectors may be comprised in the integrated sensors of the sensor array. Depending upon the type of singles to be detected, various types of detectors may be used, for example, optical detectors, electrical detectors, electrochemical detectors, or electrostatic detectors. Examples of optical detectors may include but not limited to charge-coupled device (CCDs) arrays (including cooled CCDs), complementary metal-oxide-semiconductor (CMOS) imagers, n-type metal-oxide semiconductor (NMOS), active-pixel sensors (APS), or photomultiplier tubes (PMTs). The detectors can also include wavelength-selective components such as optical filters to allow measurement of selective wavelengths. Examples of other detectors may include electrodes.

The detector can sample (e.g., acquire measurements) at a rate of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, 300, 400, 500, 1000, 10,000, or 100,000 times per minute. The detector can sample at a rate of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 15, 20, 25, 30, 35, 40, 45, 50, 55, 60, 65, 70, 75, 80, 85, 90, 95, 100, 105, 110, 115, or 120 Hz.

The detection system can comprise a light source. The light source can comprise at least one lamp, such as an incandescent, halogen, fluorescent, gas-discharge, arc, or light emitting diode (LED). The light source can comprise a laser. The light source can produce a specific wavelength or range or wavelengths, such as UV. The light source can comprise filters for controlling the output wavelength or wavelengths. The light source can comprise multiple light sources, of the same or of different types, which can be used separately or in combination.

The detector can comprise various optical elements, including but not limited to filters, lenses, collimators, mirrors, reflectors, beam splitters, and diffusers. The detector can comprise a filter or a plurality of filters, including but not limited to wavelength filters (e.g., color filters, UV filters, IR filters), dichroic filters, and polarizing filters. The filters can comprise multiple filters, of the same or of different types, which can be used separately or in combination. The detector can comprise elements (e.g., signal processing unit) for removing image distortion or aberration, such as barrel or fisheye distortion, pincushion distortion, mustache distortion, monochromatic aberrations (e.g., piston, tilt, defocus, spherical aberration, coma, astigmatism, field curvature, image distortion), or chromatic aberrations (e.g., axial, longitudinal, lateral, transverse). Such elements can comprise computer systems programmed to implement instructions for partially or fully correcting image distortion. For example, Brown's distortion model or the Brown-Conrady model can be used to correct for radial distortion and tangential distortion. In some examples, the detector can measure emitted photons coming from individual addressable locations. These photons can be correlated to the presence and/or activity of reporter molecules in that location.

As discussed elsewhere herein, parallel detection of nucleic acid (e.g., DNA) hybridization reactions as a function of temperature in real time can be performed by interaction between an immobilized probe labeled with an energy donor (e.g., a fluorophore) at a specific pixels and a target labeled with an energy acceptor (e.g., a quencher) that is present in the reaction chamber. Detection can also be performed by interaction between an intercalator and interacting probes and targets in a similar setting. The temperature of the reaction chamber can be varied, while an optical detector continually measures the signal in real time, to capture the amount of hybridized targets at individual pixels and evaluate whether the hybridization reaction is favorable or not in that given temperature at that pixel.

In some cases, signals that signify hybridization reactions are only generated at, and are confined to the pixels of the addressable array while the reaction volume which includes all the targets creates minimum background optical signal. This unique characteristic not only improve the detectable signal-to-interference (or signal-to-noise), but also enables multiplexing capabilities as the pixel-level measurements remains independent of one another. This is despite the fact that the reaction chamber and aqueous sample is shared among all of them.

Figure 2:
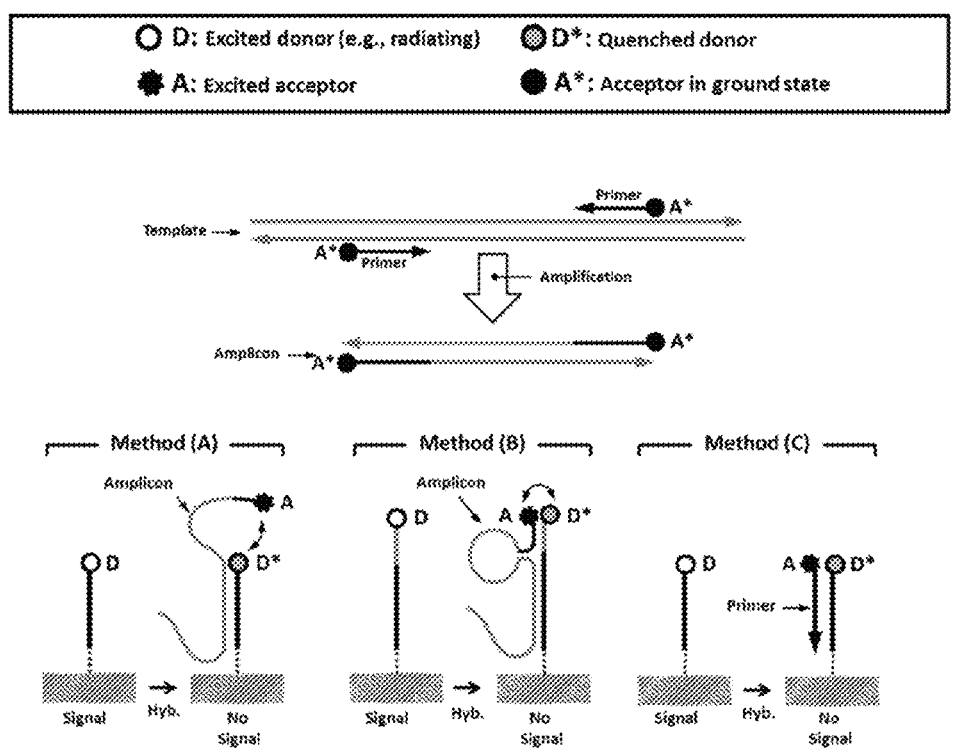
FIG. 2 schematically illustrates an example optical detection method comprising primer labeling.
Figure 3:
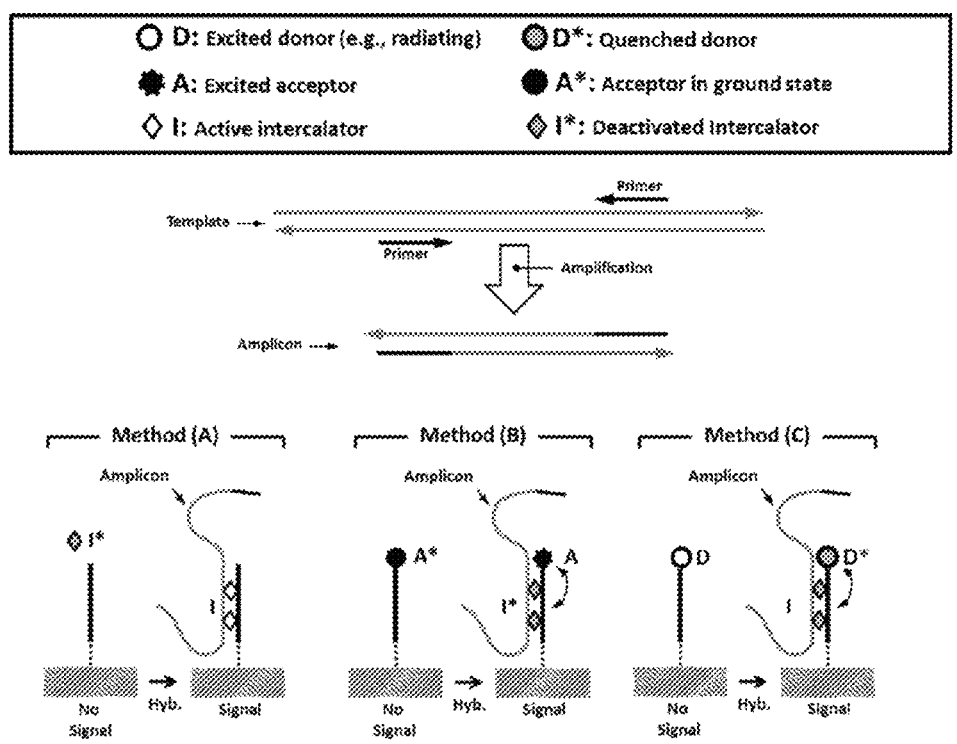
FIG. 3 schematically illustrates an example optical detection method comprising non-labeled amplicons.
Figure 4:
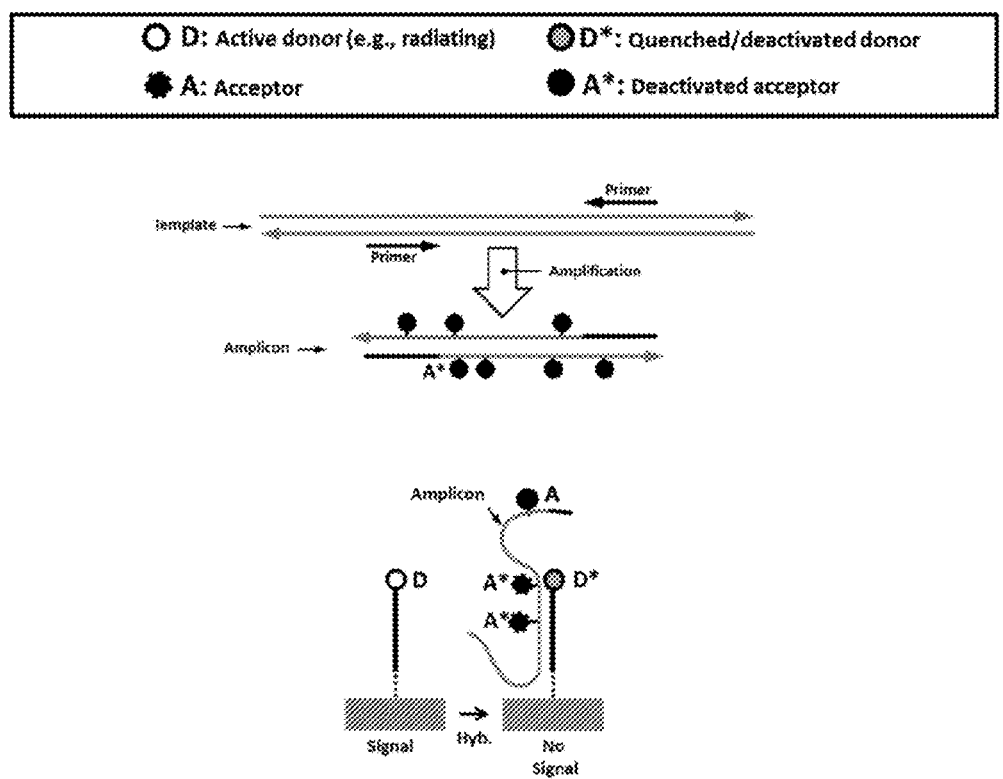
FIG. 4 schematically illustrated an example optical detection method comprising acceptor-labeled deoxynucleotide triphosphates (dNTPs)

FIGS. 2-4 illustrate exemplary optical detection methods of the present disclosure. As shown in FIG. 2, primers to be used for the following amplification reaction may be labeled with reporter molecules (e.g., energy acceptors, donors, and/or quenchers). As the amplification reaction proceeds, the reporter molecules may be incorporated into the amplified products (i.e., amplicons). Progress of the amplification reaction may be monitored in real-time by detecting the change of signals upon the hybridization/binding of the amplicons or primers to the probes. In example method A, prior to binding, the donor on the probe is actively radiating signal. Once the probe binds to the target (i.e., quencher-labeled amplicon), the quencher bound to the target quenches the signal from the energy donor bound to the probe, which results in a decrease or disappearance of the signal. In example method B, energy donor-labeled probe keeps emitting/radiating signals until binding between the acceptor-incorporated amplicon and the probe occurs. A hairpin structure may be formed in the amplicon to facilitate the binding between the amplicon and the probe. Once the hybridization/binging is completed, a reduction in energy donor signal may be detected, indicating the ongoing of the amplification reaction. In method C, instead of binding to the amplified products, the probe is designed and configured to bind to the primers. The binding between the primer and the probe may result in a reduction of signal produced by the donor-labeled probe prior to the binding. As the amplification reaction proceeds, more primers may be consumed. Such decrease in the amount of primers free in the solution may be detected and hence indicative of the progress of the reaction.

As discussed elsewhere herein, in some cases, the detection of target substances may be realized via the use of other molecules, for example, an intercalator. Under such circumstances, no labeling for primer or amplicon is required, which greatly diminishes the background noises produced from the reaction solution. As shown in FIG. 3, in method A, the intercalator is inactive and produces little to no signal in the absence of the binding. Once the hybridization/binding occurs between the unlabeled amplicon and the probe, the intercalator becomes activated and radiates a signal. In method B, the probe may be labeled by a deactivated energy acceptor which without binding to target substances produces little to no signal. The binding between the probe and the amplicon may then bring the intercalator and the deactivated acceptor into close proximity. The energy transfer between the intercalator and the acceptor may result in an increase of the signal. In method C, a probe is labeled with a donor and there may be deactivated acceptors freely-moving in the solution. Prior to the binding of an amplicon to the probe, the donor on the probe may be actively radiating signal due to the large distance between the donor and acceptor. The binding of the amplicon to the probe may bring the acceptors in close proximity to the energy donor on the probe, resulting in a decrease or disappearance of the signal.

FIG. 4 shows an example optical detection method by using labeled dNTP. As FIG. 4 shows, one or more dNTPs may be labeled with a reporter molecule, for example, an acceptor. As the amplification reaction proceeds and the template nucleic acid sequence gets replicated and elongated, the labeled dNTPs become incorporated into the amplified products (i.e., amplicons). The amplicons may be able to bind to the probe which is labeled with a different type of reporter molecule, e.g., a donor. In cases where the probe is donor-labeled, it may produce or emit signals without binding to any other substances. The produced signals may be reduced or diminished once the amplicon binds to the probe.

Figure 5:
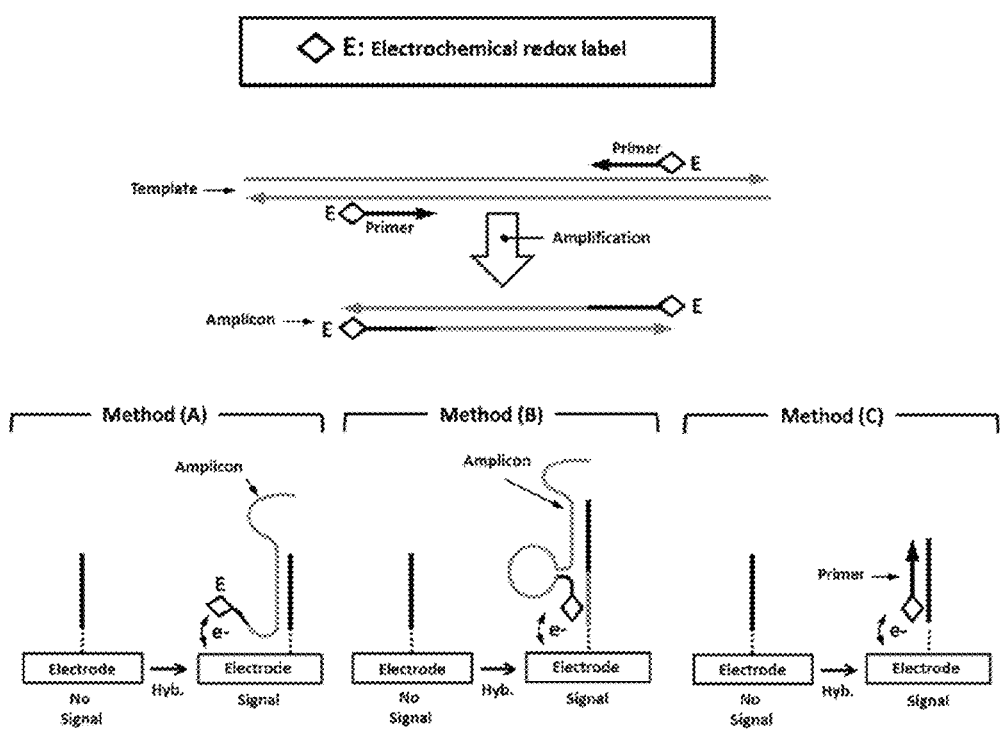
FIG. 5 schematically illustrates an example electrical detection method comprising primer labeling.
Figure 6:
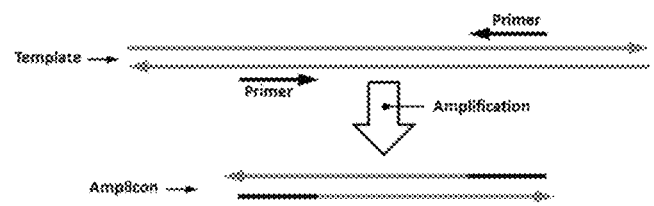
FIG. 6 schematically illustrates an example electrical detection method comprising non-labeled amplicons.
Figure 6:
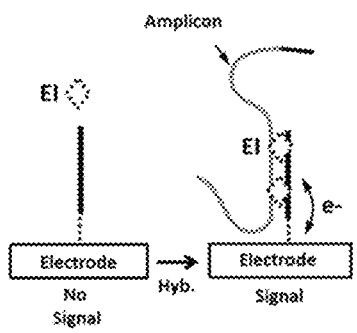
Figure 7:
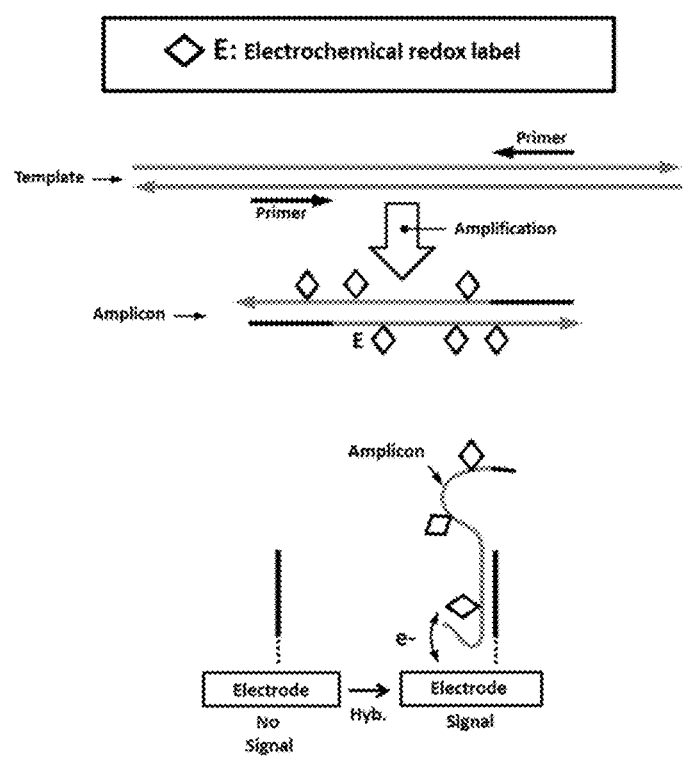
FIG. 7 schematically illustrated an example electrical detection method comprising redox-labeled deoxynucleotide triphosphates (dNTPs)

FIGS. 5-7 show exemplary electrical detection methods of the present disclosure. In such methods, target substances (e.g., primers, amplicons, dNTPs) and/or probes may be labeled by one or more reporter molecules (e.g., redox species) that are capable of producing or generating electrical signals to be detected by the detection system. In some cases, neither the target substances nor the probes are labeled with the reporter molecules and the signal may be generated with the use of other molecules, for example, an intercalator. For methods and systems that utilize electrical detection methods, one or more electrodes may be used to acquire the signals. The electrodes may be separated from or associated with the probe array. The electrodes may be integrated with the probe array and/or the detection system. The electrodes may be further integrated with a computer control system that is configured to implement the methods provided herein. In some cases, the electrodes may be embedded in the substrate of the probe array and correspond to each of the addressable locations (e.g., pixels) of the array. The signals produced from each of the locations may be real-time detected and/or monitored in parallel.

FIG. 5 shows an example electrical detection method by using labeled primers. As the figure shows, the primers may be labeled with redox species which may then be incorporated into the amplified products once the amplification reaction starts. In method A, prior to the binding, the probe produces little to no signals. As the amplification reaction proceeds and the amplicon starts to bind to the probe, the hybridization/binding of the amplicon result in an increase of the signal, which in turn indicates the progress of the amplification reaction. In method B, a hairpin structure may be formed in amplicon to facilitate the binding between the amplicon and the probe. Or, the formation of the hairpin loop may be required to bring the amplicon and the probe into close proximity such that a detectable signal may be produced once the binding occurs. By detecting the signal change and/or intensities, the progress and/or degree of the amplification reaction can be determined. In method C, a labeled primer instead of an amplicon is captured or bound to the probe. The quantity or amount of the primers in the reaction mixture can be easily determined by monitoring the change of signal intensities generated via the binding between primers and probes. A decrease in the quantity or amount of the primers may then be reflective of the progress of the amplification reaction.

For methods illustrated in FIG. 6, no labeling is required. As shown in this figure, prior to the binding, an electrochemical intercalator is free-flowing in the reaction mixture and produces little to no signal(s), and little to no reporter molecules are comprised in probes and amplicons. Therefore, before the binding occurs, no signals can be detected from the reaction mixture. As the amplification reaction proceeds and the amplicon begins to bind to the probe, the intercalator may be activated and start to produce signals for detection.

As provided elsewhere herein, any substances in reaction mixture may be labeled with one or more reporter molecules. In method shown in FIG. 7, dNTPs may be labeled by reporter molecules (e.g., electrochemical redox labels). These labels may be incorporated into amplicons later on as the amplification reaction proceeds. As shown in FIG. 7, prior to the binding, the probe produces little to no signals. Once the hybridization/binding occurs, signals may be produced and detected.

System of the present disclosure may comprise an integrated biosensor array having a plurality of integrated biosensors. An example advantage of using integrated biosensors, rather than conventional detection apparatuses, is the drastic reduction is size and lower cost. Furthermore, integrated biosensor arrays can be manufactured using semiconductor integrated circuit (IC) micro-fabrication processes, e.g., complementary metal-oxide-semiconductor (CMOS), which can offer unmatched reliability, high-volume manufacturing, and reliability. Examples of sensors that may be used with integrated biosensors arrays of the present disclosure are provided in U.S. Patent Pub. Nos. 2010/0122904, 2013/0345065, 2014/0001341, 2014/0318958, 2014/0011710, 2012/0168306, 2013/0225441, 2012/0077692, 2007/0099198, 2008/0081769, 2008/0176757 and 2008/0039339, and U.S. Pat. Nos. 8,637,436, 8,048,626, and 8,518,329, each of which is entirely incorporated herein by reference.

In such arrangements, each sensor element can be addressable and can include its own probe. Such sensor element may be a biosensor. The array can comprise a number of individual biosensors, such as at least about 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000, or 100000 integrated biosensors. The density of individual biosensor in the array can be at least about 100, 200, 300, 400, 500, 1000, 2000, 3000, 4000, 5000, 6000, 7000, 8000, 9000, 10000 biosensor pixels per $mm^2$.

A biosensor in the array can comprise a photo-sensor, such as a photodiode. Each biosensor can also be associated with temperature control elements as well, such as heaters and temperature sensors (e.g., thermocouples, thermistors). The biosensor array can comprise optical filters, such as emission filters, between the photo-sensors and the reaction chambers or array pixels as described in, for example, in U.S. Patent Pub. Nos. 2010/0122904, 2013/0345065, 2014/0001341, 2014/0318958, 2014/0011710, 2012/0168306, 2013/0225441 and 2008/0081769, and U.S. Pat. Nos. 8,637,436 and 8,518,329, each of which is entirely incorporated herein by reference.

Figure 10:
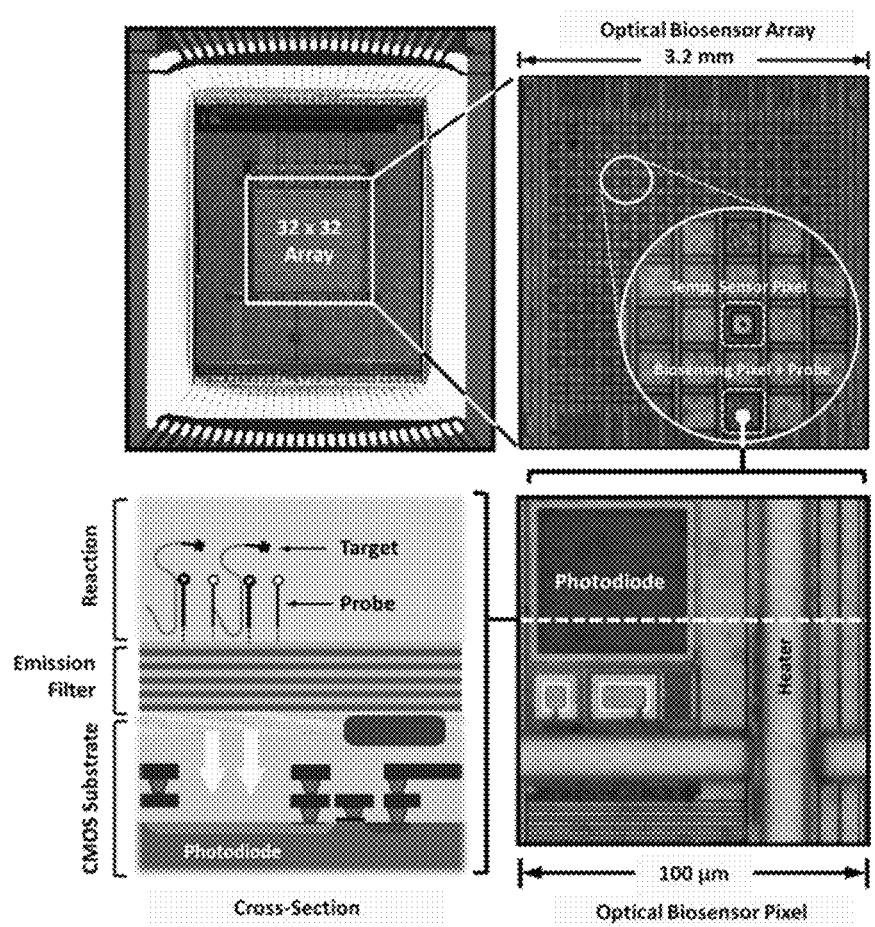
FIG. 10 shows example images and a schematic of an optical biochip detector.

FIG. 10 shows an optical CMOS biochip detector (FIG. 10, top left) comprising a 32 by 32 array of optical biosensors (FIG. 10, top right). Each optical biosensor is about 100 micrometers square ($mm^2$). Each side of the optical biosensor array is about 3.2 mm in length. Each biosensor comprises a photodiode sensor, and an emission filter is located between the CMOS substrate of the biosensor and the reaction chamber of the associated array pixel (FIG. 10, bottom left). The heat of the array can be controlled by heaters (FIG. 10, bottom right).

Figure 11:
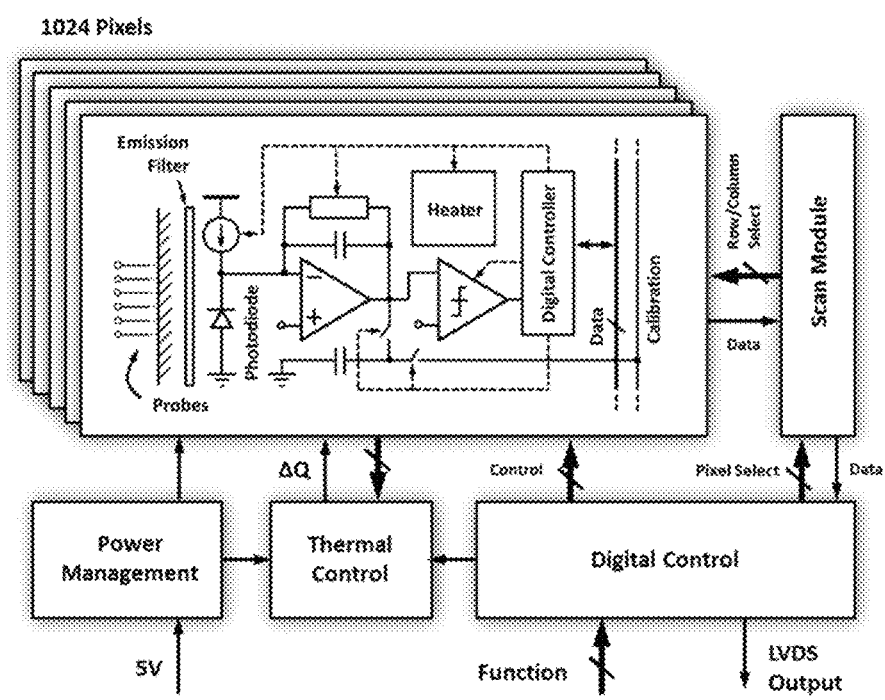
FIG. 11 shows an example optical biochip circuit architecture.

FIG. 11 shows example circuit architecture for an optical CMOS biochip. Each of the 1024 pixels comprises a reaction chamber associated with a photodiode circuit, separated by an emission filter. Each pixel further comprises a heater, a digital controller, and signal input/output for calibration and data collection. The biochip further comprises a digital controller. The digital controller interfaces with a scan module capable of row/column selection of biochip pixels for receiving data. The digital controller also interfaces with a thermal controller capable of controlling the on-chip temperature. A power management system (e.g., 5 volts) provides power to the pixels and the thermal controller.

Figure 12:
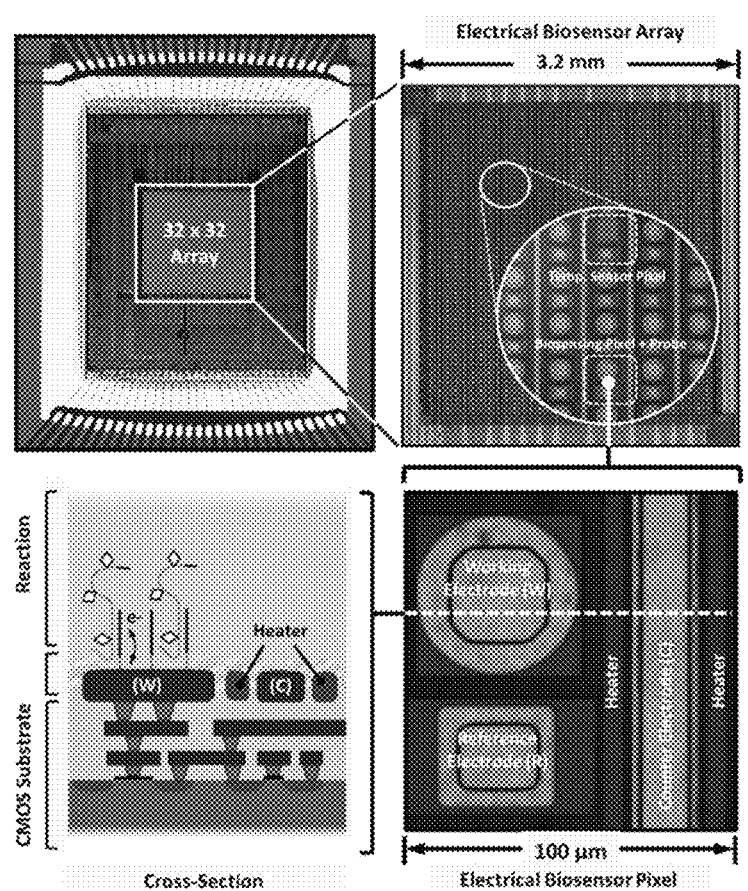
FIG. 12 shows example images and a schematic of an electrical biochip detector.

An electrical CMOS biochip detector is shown in FIG. 12. The example biochip detector (FIG. 12, top left) comprises a 32×32 array of electrical biosensors (FIG. 12, top right). Each electrical biosensor is about 100 micrometers square ($mm^2$). Each side of the biosensor array is about 3.2 mm in length. Each biosensor comprises a probe array located between the CMOS substrate of the biosensor and the reaction chamber of the associated array pixel (FIG. 12, bottom left). Each of the biosensors may comprise a reference electrode (R) underneath a working electrode (W), a counter electrode (C) disposed in between two heater layers. The heat of the array can be controlled by heaters (FIG. 12, bottom right).

Figure 13:
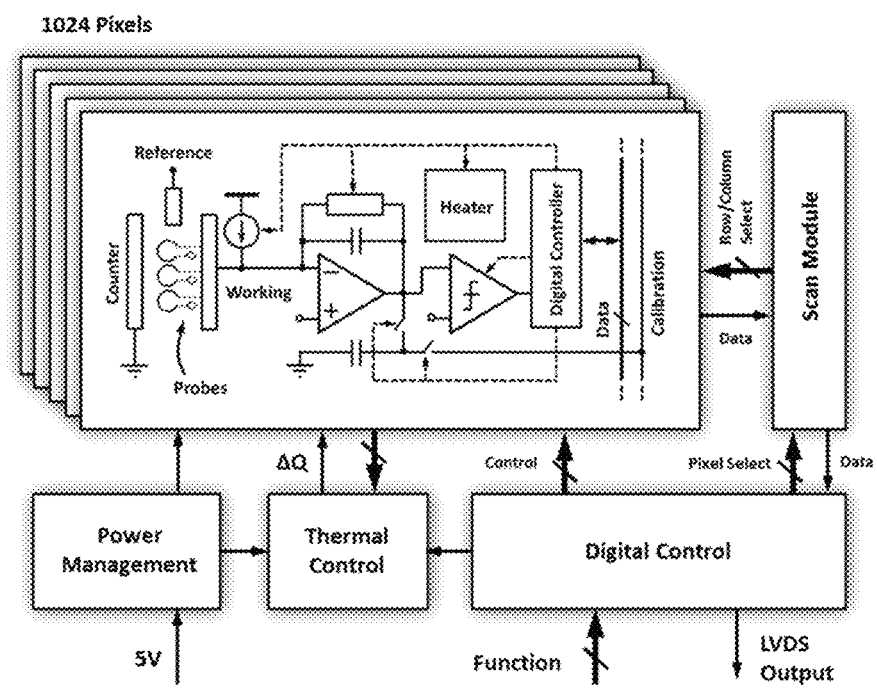
FIG. 13 shows an example electrical biochip circuit architecture.

Example circuit architecture for an electrical CMOS biochip is shown in FIG. 13. As the figure shows, each of the 1024 pixels comprises a reaction chamber associated with an electrical detection circuit having a working electrode, a reference electrode and a counter electrode. Each pixel further comprises a heater, a digital controller, and signal input/output for calibration and data collection. The biochip further comprises a digital controller. The digital controller interfaces with a scan module capable of row/column selection of biochip pixels for receiving data. The digital controller also interfaces with a thermal controller capable of controlling the on-chip temperature. A power management system (e.g., 5 volts) provides power to the pixels and the thermal controller.

Nucleic Acid Amplification

Methods, devices and systems provided herein can be used for performing nucleic acid amplification reaction on a plurality of nucleotide sequences in a fluid that is in contact with an array of probes disposed in a plurality of independently addressable locations. The presence, quantity and/or binding activity of the amplified products (i.e., amplicons) within each probe-comprising addressable location may be simultaneously detected and monitored in real-time as the reaction proceeds. Methods of amplification may include, for example, polymerase chain reaction (PCR), strand displacement amplification (SDA), and nucleic acid sequence based amplification (NASBA), and Rolling Circle Amplification (RCA).

The amplification method can be temperature cycling or be isothermal. The amplification method can be exponential or linear. For amplifications with temperature cycling, a temperature cycle may generally correspond to an amplification cycle. Isothermal amplifications can in some cases have amplification cycles, such as denaturing cycles, and in other cases, the isothermal amplification reaction will occur monotonically without any specific amplification cycle.

The amplification method may be used to amplify specific regions (i.e., target regions), or nucleotide sequences of a nucleic acid molecule (e.g., DNA, RNA). This region can be, for example, a single gene, a part of a gene, or a non-coding sequence.

The amplification method may comprise: (1) a template that contains the region of the nucleic acid sequence to be amplified; (2) one or more primers, which are complementary to the target region at the 5' and 3' ends of the region that is to be amplified; (3) a polymerase (e.g. Taq polymerase), used to synthesize a copy of the region to be amplified; (4) deoxynucleotide triphosphates (dNTPs); (5) a buffer solution, which provides a suitable chemical environment for optimum activity and stability of the polymerase; and/or (6) a divalent cation such as magnesium or manganese ions.

A primer may be a nucleic acid strand, or a related molecule that serves as a starting point for nucleic acid replication. A primer may often be required because some nucleic acid polymerases cannot begin synthesizing a new strand from scratch, but can only add to an existing strand of nucleotides. The length of the primers may vary. Primers with longer or shorter lengths may be used, dependent upon, the application. For example, in some cases, chemically synthesized DNA molecules with a length about 10 to about 30 bases may be used as primers. In some cases, the length of primers can be for example about 20-30 nucleotides, and the sequence of the primers are complementary to the beginning and the end of the target fragment to be amplified. The primers may anneal (adhere) to the template at these starting and ending points, where polymerase binds and begins the synthesis of the new strand. In some cases, degenerate primers may be used. Degenerate primers comprise mixtures of similar, but not identical, primers.

In some cases, asymmetric (or non-symmetric) amplification processes (e.g., asymmetric PCR) may be utilized. A primer pair compressing a limiting primer and an excess primer may be used in an asymmetric amplification process. The limiting primer may be present at a much lower concentration than the excess primer. The asymmetric amplification processes may preferentially amplify one strand in a double-stranded nucleic acid template by using an excess of a primer for the strand targeted for amplification. As the amplification reaction progresses, the limiting primer may be used up.

As provided in the present disclosure, primers may or may not be labeled with a reporter molecule (e.g., a label). The labeled primers may be configured to facilitate and/or enable the detection and/or monitoring of the presence, quantity, concentration or binding activity of the primers, amplicons, or other analytes. The reporter molecule may be incorporated into the amplified products as the amplification reaction proceeds. The primers may be labeled with one or more reporter molecules. The reporter molecules can be optical, electrical or electrochemical. Examples of reporter molecules may include, but not limited to fluorescent, quenchers, fluorophores, members of a fluorescence resonance energy transfer (FRET) pair, redox species, or combinations thereof.

In cases where an asymmetric amplification process is utilized, each primer in a primer pair may be labeled with the same or a different type of reporter molecules. As described elsewhere herein, the systems, devices and methods of the present disclosure may comprise an array having a plurality of independently addressable locations (e.g., pixels). Each of the addressable locations may or may not contain one or more probes that are configured to be able to capture one or more species in the reaction chamber (e.g., primers, amplicons, polymerases, dNTPs, or any other analytes and reagents). The probes may or may not be labeled by one or more reporter molecules. The labeled probes may or may not be able to produce signals (e.g., optical, electrical, electrochemical, magnetic, mechanical, acoustic, or electromagnetic signals) that can be detected or monitored by a detection system provided in the present disclosure. The detected signal may be indicative or reflective of a progress of a reaction (e.g., a nucleic acid amplification progress). In some cases, each of the addressable locations may comprise the same type of probes, for example, probes that are capable to capture a specific target nucleic acid sequence. In some cases, it may be preferred to have an array in which each of the addressable locations contains a different type of probes. Each type of the probes may be used to specifically capture and therefore detect/monitor a certain type of target substances (e.g., a primer, an amplicon etc.) as the reaction progresses. In some cases, it may be useful to have at least two different types of probes that are able to capture and/or detect at least two different type of target substances.

Figure 8:
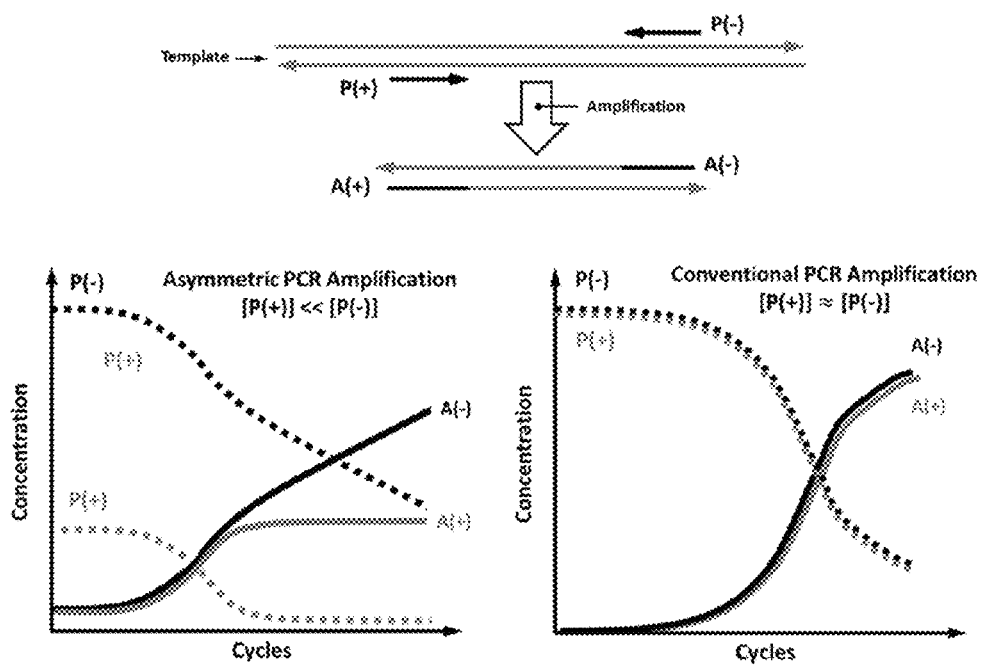
FIG. 8 shows concentration of primers and amplicons in an example asymmetric PCR amplification and a conventional PCR amplification methods.

Example amplification methods of the present disclosure, along with concentration profiles of primers and amplicons in the methods are shown in FIG. 8. As FIG. 8 shows, in amplification reaction, a primer pair is used. Depending upon, whether there is a difference between concentrations of the primers, an asymmetric PCR amplification or a conventional amplification method may be utilized. For example, if for two primers in a pair, [P(+)] is the same or substantially the same as [P(−)], then a convention amplification reaction is conducted. However, if the concentration of one primer is largely different from the other one in the pair, for example, [P(+)]<<[P(−)], then an asymmetrical amplification method is used. As described elsewhere herein, the quantity, amount, and/or concentration of one or more target substances contained in reaction mixture (e.g., primers, amplicons, dNTPs) may be detected or monitored in real-time with the methods and systems of the present disclosure. By following or monitoring the quantity/concentration change of at least one substance, the progress of the amplification reaction may be determined (FIG. 8, bottom left and bottom right).

A wide variety of fluorescent molecules (e.g., small molecules, fluorescent proteins and quantum dots) can be utilized in the present disclosure. Non-limiting examples of fluorescent molecules (or fluorophores) may include: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—utoFluorescent Protein—(Quantum Biotechnologies); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexion; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FI; Bodipy FL ATP; Bodipy FI-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-SN; Calcein; Calcein Blue; Calcium Crimson™; Calcium Green; Calcium Green-1 Ca.sup.2+Dye; Calcium Green-2 Ca.sup.2+; Calcium Green-SN Ca.sup.2+; Calcium Green-C18 Ca.sup.2.sup.+; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); Dil (DiIC18(3)); Dinitrophenol; DiO (DiOC18 (3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby); Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium lodid (PL); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; WW 781; X-Rhodamine; XRITC; Xylene Orange; Y66F; Y66H; Y66 W; YO-PRO-1; YO-PRO-3; YOYO-1; YOYO-3, Sybr Green, Thiazole orange (interchelating dyes), Alexa Fluor dye series (e.g., Alexa Fluor 350, Alexa Fluor 405, 430, 488, 500, 514, 532, 546, 555, 568, 594, 610, 633, 635, 647, 660, 680, 700, and 750), Cy Dye fluorophore series (e.g., Cy3, Cy3B, Cy3.5, Cy5, Cy5.5, Cy7), Oyster dye fluorophores (e.g., Oyster-500, -550, -556, 645, 650, 656), DY-Labels series (e.g., DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL), ATTO fluorescent labels (e.g., ATTO 390, 425, 465, 488, 495, 520, 532, 550, 565, 590, 594, 610, 611X, 620, 633, 635, 637, 647, 647N, 655, 680, 700, 725, 740), CAL Fluor and Quasar dyes (e.g., CAL Fluor Gold 540, CAL Fluor Orange 560, Quasar 570, CAL Fluor Red 590, CAL Fluor Red 610, CAL Fluor Red 635, Quasar 670), quantum dots (e.g., Qdot 525, Qdot565, Qdot585, Qdot605, Qdot655, Qdot705, Qdot 800), fluorescein, rhodamine, phycoerythrin, or combinations thereof.

Molecules that can be used in FRET may include fluorophores as described above, fluorescein, 5-carboxyfluorescein (FAM), 2'7'-dimethoxy-4'5'-dichloro-6-carboxyfluorescein (JOE), rhodamine, 6-carboxyrhodamine (R6G), N,N, N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl) aminonaphthalene-1-sulfonic acid (EDANS).

In some cases, the acceptor of the FRET pair may be used to quench the fluorescence of the donor. The acceptor may have little to no fluorescence. In some cases, the FRET acceptors that are useful for quenching may be referred to as quenchers. Non-limiting examples of quenchers may include, Black Hole Quencher Dyes (e.g., BHQ-0, BHQ-1, BHQ-2, BHQ-3, BHQ-10), QSY Dye fluorescent quenchers (e.g., QSY7, QSY9, QSY21, QSY35), Dabcyl and Dabsyl, Cy5Q, Cy7Q, Dark Cyanine dyes (which can be used, for example, in conjunction with donor fluors such as Cy3B, Cy3, or Cy5), DY-Quenchers (e.g., DYQ-660 and DYQ-661), ATTO fluorescent quenchers (e.g., ATTO 540Q, 580Q, 612Q), or combinations thereof.

Target Substance/Probe Binding

Methods, devices and systems provided herein may be utilized to measure, monitor and/or detect the hybridization or binding characteristics of multiple target substances (e.g., amplicons, primers, dNTPs, or any other reagents and/or analytes) to multiple probes in real-time. The probes may be configured and/or designed such that one or more type of target substances may specifically bind or hybridize to one or more types of probes. As used herein, a probe "specifically binds" to a specific target molecule if it binds to that molecule with greater affinity than it binds to other substances in the sample. As provided elsewhere herein, certain types of probes may be contained within a certain percentage of independently addressable locations and upon binding of target substances to the probes within the locations, signals detected or collected therefrom may be indicative or reflective of the presence, amount, quantity, activity, and/or binding characteristics of specific types of substances.

The binding between the probes and the target substances may occur in solution (e.g., an aqueous solution). The binding between the target substances and the probes and the signal detection can occur concurrently or sequentially. For example, in some cases, the binding between the probes and the target substances may occur prior to the detection of the signals.

In some cases, the probe and the target substances may specifically bond to each other by hybridization. In some cases the binding can be through other molecular recognition mechanisms. Molecular recognition may involve detecting binding events between molecules. The strength of binding can be referred to as "affinity". Affinities between biological molecules may be influenced by non-covalent intermolecular interactions, for example, hydrogen bonding, hydrophobic interactions, electrostatic interactions and Van der Waals forces. In multiplexed binding events, a plurality of target substances and probes may be involved. For example, in some cases, bindings between a plurality of different nucleic acid molecules and/or different proteins may be tested. In such cases, it may be preferred to have target substances preferentially bind to probes for which they have greater binding affinities. Thus, determining that a particular probe is involved in a binding event may indicate the presence of a target substance in the sample that has sufficient affinity for the probe to meet the threshold level of detection of the detection system being used. One may be able to determine the identity of the binding partner based on the specificity and strength of binding between the probe and the substance.

The specific binding can be, for example, a receptor-ligand, enzyme-substrate, antibody-antigen, or a hybridization interaction. The probe/target substance binding pair can be nucleic acid to nucleic acid, e.g. DNA/DNA, DNA/RNA, RNA/DNA, RNA/RNA. The probe/target substance binding pair can be a polypeptide and a nucleic acid, e.g. polypeptide/DNA and polypeptide/RNA, such as a sequence specific DNA binding protein. The probe/target substance binding pair or can be any nucleic acid and synthetic DNA/RNA binding ligands (such as polyamides) capable of sequence-specific DNA or RNA recognition. The probe/target substance binding pair can comprise natural binding compounds such as natural enzymes and antibodies, and synthetic binding compounds. The probe/target substance binding can comprise aptamers, which are nucleic acid or polypeptide species that have been engineered to have specific binding properties, usually through repeated rounds of in vitro selection or equivalently, SELEX (systematic evolution of ligands by exponential enrichment).

The hybridization or binding may result in a change in signal. The signal may be related to (e.g., proportional to) the amount of hybridized or bound substances. For example, an assay where a 5 fold difference in concentration of the target substances may result in a 3 to 6 fold difference in signal intensities. The signal may be related to the binding affinities between the probes and the target substances. The signal intensity may be used to discriminate between different types of target substances. Control samples may or may not be tested and compared to the target substances to be detected. In cases where more precise quantification is required, controls may be run to correct for variations introduced in sample preparation and hybridization as described herein.

Computer Control System

Figure 19:
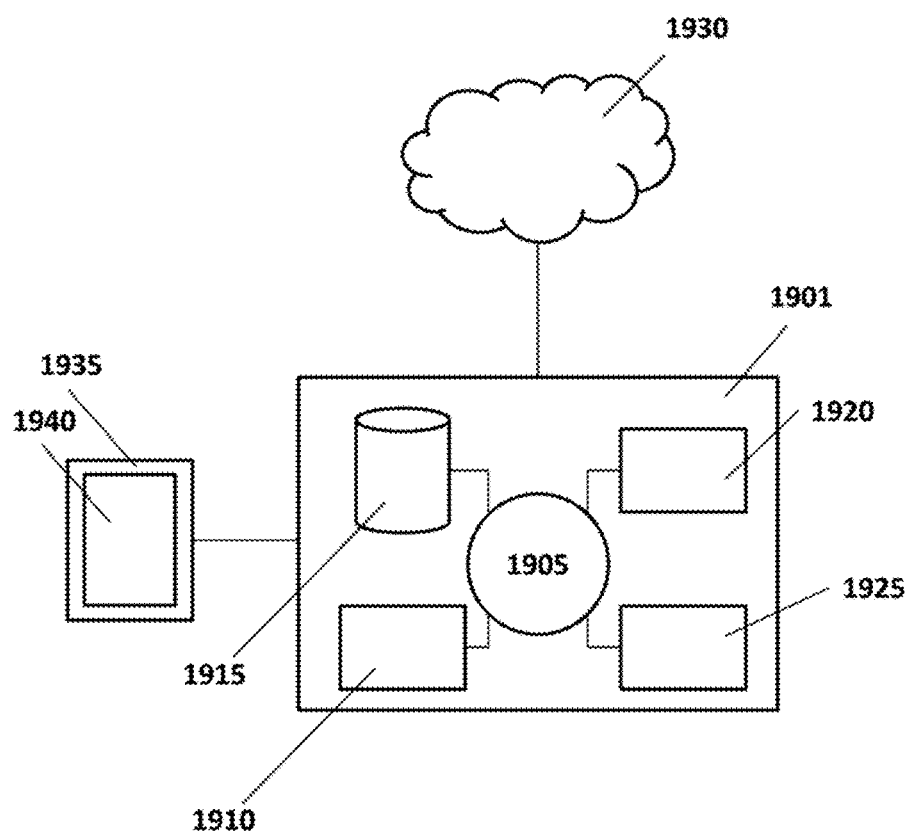
FIG. 19 shows an example computer control system that is programmed or otherwise configured to implement methods provided herein.

The present disclosure provides computer control system that is programmed to implement methods of the disclosure. FIG. 19 shows a computer system 1901 that is programmed or otherwise configured to perform various functions of the methods and systems of the present disclosure, for example, performing an amplification reaction, real-time detecting and/or monitoring the binding of target substances (e.g., primers, amplicons) to an array of probes, identifying a threshold cycle ($C_t$) of an amplification reaction, and/or monitoring the progress of a reaction. The computer system 1901 can regulate various aspects of simultaneously performing at least one amplification reaction and detecting changes in signals produced by the probe array, such as, for example, temperature control, reagent handling, and signal detection. The computer system 1901 can be intergraded with the systems provided in the present disclosure.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet. The network 1930 in some cases is a telecommunication and/or data network. The network 1930 can include one or more computer servers, which can enable distributed computing, such as cloud computing. The network 1930, in some cases with the aid of the computer system 1901, can implement a peer-to-peer network, which may enable devices coupled to the computer system 1901 to behave as a client or a server.

The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user (e.g., a lab technician, a physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface (UI) 1940 for providing, for example, cycle numbers, temperature values, temperature control, detector data, and reagent handling. Examples of UI's include, without limitation, a graphical user interface (GUI) and web-based user interface. Methods and systems of the present disclosure can be implemented by way of one or more algorithms. An algorithm can be implemented by way of software upon execution by the central processing unit 1905. The algorithm can, for example, control the temperatures of each of the addressable locations, collect signals and analyze collected data.

EXAMPLES

Example 1

Threshold Cycle ($C_t$) Identification

Figure 9A:
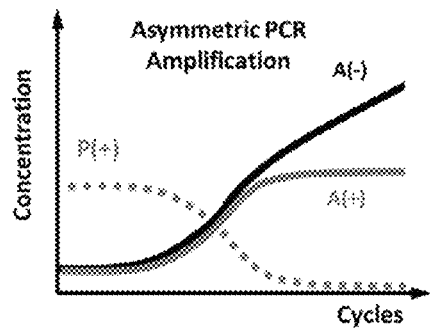
FIGS. 9A-9D show signals measured and threshold cycle ($C_t$) identified in an example asymmetric PCR amplification and a conventional PCR amplification methods.
Figure 9C:
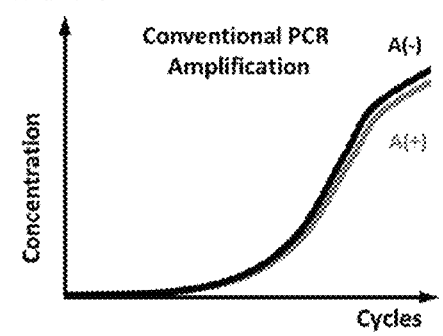
Figure 9B:
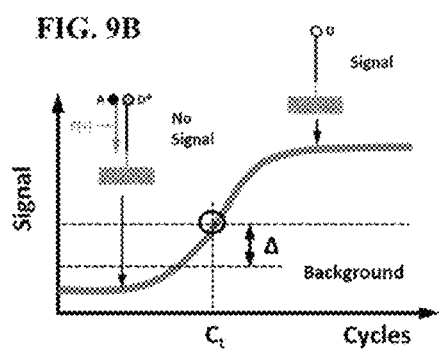
Figure 9D:
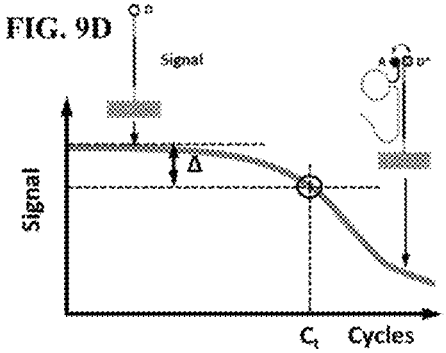

Threshold cycle ($C_t$), the intersection between an amplification curve and a threshold line and a relative measure of the concentration of a target substance in an amplification reaction, can be measured with the methods, devices and systems of the present disclosure. The left and right two plots in FIGS. 9A-9D illustrate the determination of $C_t$ in an example asymmetric amplification reaction and a conventional amplification reaction respectively. In asymmetric amplification reaction (FIGS. 9A and 9B), a limiting primer is utilized, i.e., the concentration of the limiting primer is much lower than the concentration of the other primer of the primer pair. Both primers of the primer pair may be labeled with reporter molecules (e.g., energy acceptors). As the amplification reaction proceeds, both primers in the primer pair are consumed. Due to its lower starting concentration, the limiting primer is depleted much faster than its counterpart. Some of the probes may be designed to specifically bind to the limiting primers and the signal change upon the binding between the probes and the limiting primers is indicative of the progress of the amplification reaction. As FIG. 9B shows, at the early stage of the amplification, only a few limiting primers (i.e., P(+)) participate in the amplification reaction and the binding/hybridization between the limiting primer and the probe produces little to no signals. With the progress of the amplification reaction, more and more limiting primers take part in the amplification reaction and less binding pairs (i.e., limiting primer and probe) may be found in the reaction mixture. The decrease in the number of binding pairs result in an increase of signals from the probes, and a plateau may be soon reached as the limiting primers are depleted. According to the signal change with cycle numbers, a threshold cycle ($C_t$) can easily be identified.

On the other hand, in a conventional amplification method (FIGS. 9C and 9D), a pair of primers with substantially the same concentration is utilized for amplifying the target nucleic acid sequences. In such method, a donor-labeled probe is applied. Such labeled probe may emit/generate signals prior to its binding to an amplified product. At the early stage of the amplification reaction, very few amplicons are produced and signals produced by the probes are less influenced. The amplicons then accumulate exponentially with the number of thermal cycles and bind to numerous probes. This binding between the amplicons and the probes result in a drop of signals produced by the probes. By plotting the signals with the cycle numbers, a threshold cycle ($C_t$) can be determined.

Example 2

Primer Depletion Method to Detect on-Chip Amplification Reaction

Figure 14A:
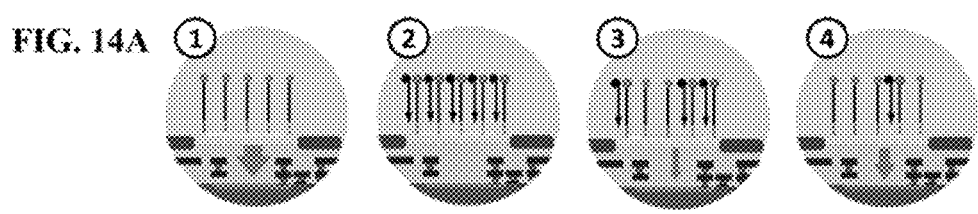
FIGS. 14A-14C show an example method of detecting on-chip PCR amplification.
Figure 14B:
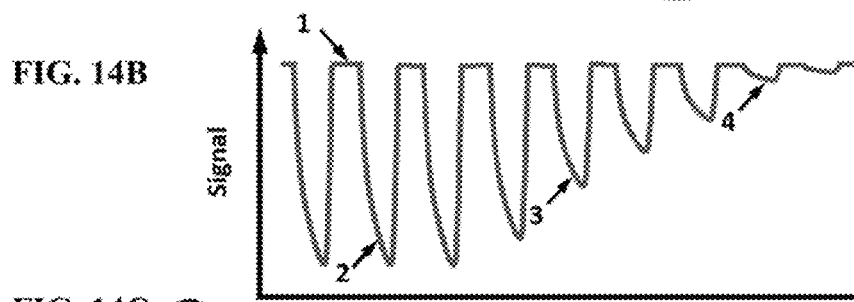
Figure 14C:
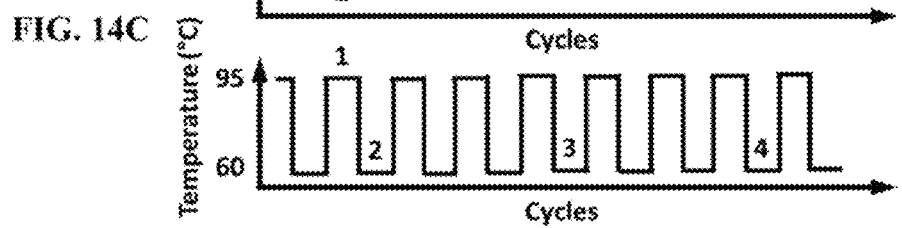

FIGS. 14A-14C shows an example primer depletion method of detecting an on-chip amplification reaction. As FIG. 14A shows, a probe array having a plurality of probes is provided. Each of the probes is labeled with a reporter molecule (e.g., an energy donor) and configured to be capable of binding to a limiting primer in a primer pair. The limiting primers may be labeled with another type of reporter molecules such that upon binding of the primers to the probes, the signals initially produced by the probes may be reduced or eliminated. As the amplification reaction proceeds, more and more limiting primers are consumed and less binding pairs may exist, which therefore causes an increase of signals detected from the probe array. As will be appreciated, the total intensities of signals detected or obtained from the probe array may be highly dependent on the number of thermal cycles. By using a thermal control module, temperature profiles of can be precisely controlled, as shown in FIG. 14C. Progress of the amplification reaction may then be monitored in real-time by detecting the total signal intensities of the probes (FIG. 14B).

Figure 15:
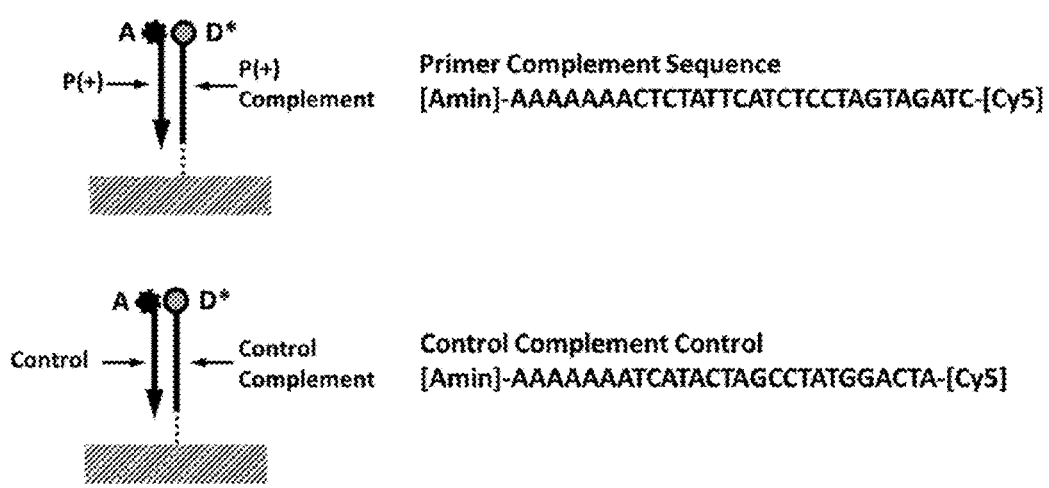
FIG. 15 shows example primer-complement and control-complement sequences (SEQ ID NOS 1 and 2, respectively, in order of appearance)

FIGS. 15-18 show example data obtained by a primer depletion method of the present disclosure. As illustrated in FIG. 15, at least two kinds of probes are utilized, each of which can specifically bind to a primer sequence and a control sequence. The control sequence is designed in such a way that it does not participate in the amplification reaction thus the signals produced by control sequence-probe binding pair is independent of the progress of the amplification reaction.

Figure 16:
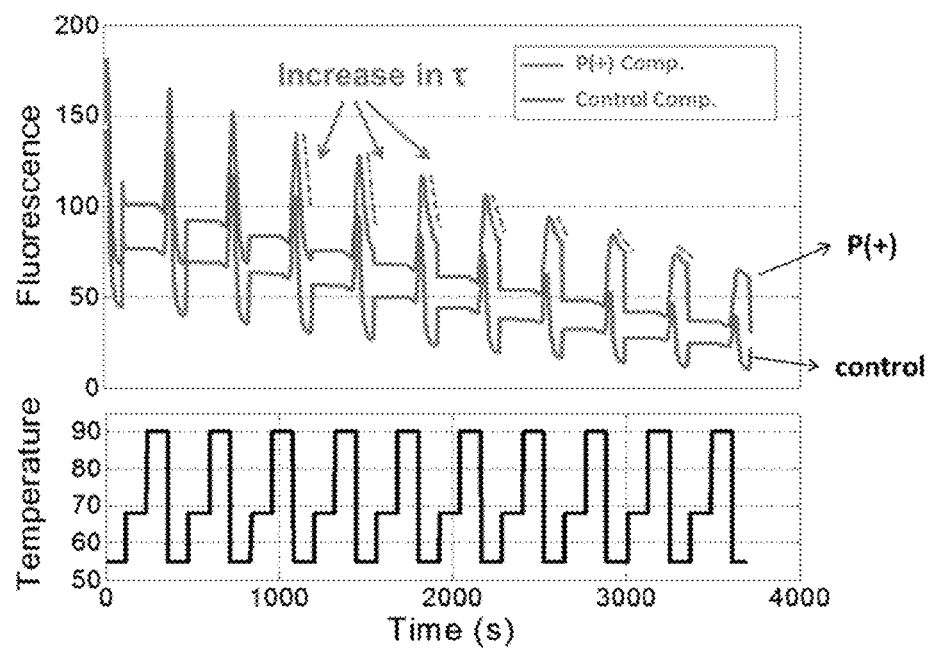
FIG. 16 shows data measured in an example array.
Figure 17:
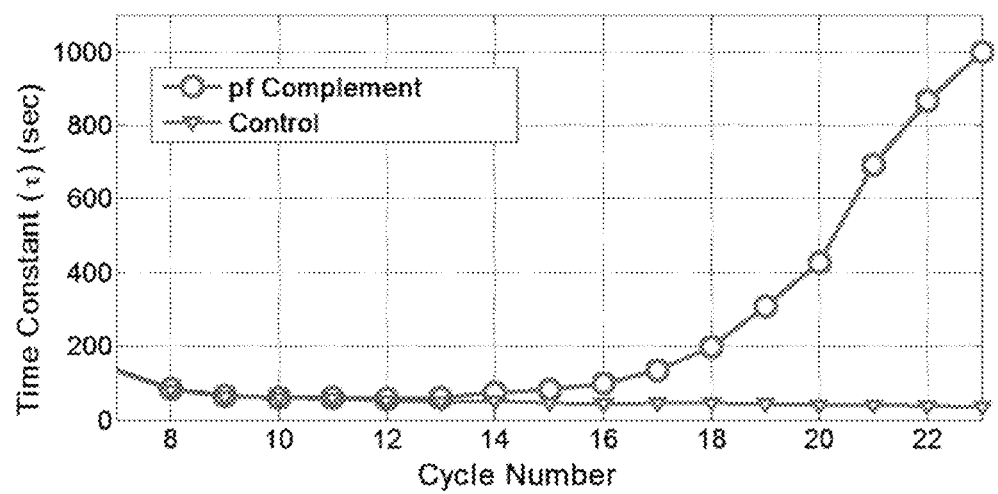
FIG. 17 shows amplification data measured in an example array.

FIG. 16 shows the time dependence of fluorescence detected and temperature of the amplification reaction. As shown in FIG. 16, a decrease of fluorescent signal detected for the control sequences is due to the photobleaching. While for primer sequences, an increase in time constant $\tau$ is observed, which may be due to the lowering of primer concentrations. By plotting the measured time constant $\tau$ against the cycle number, the progress of the amplification reaction can be monitored.

Figure 18:
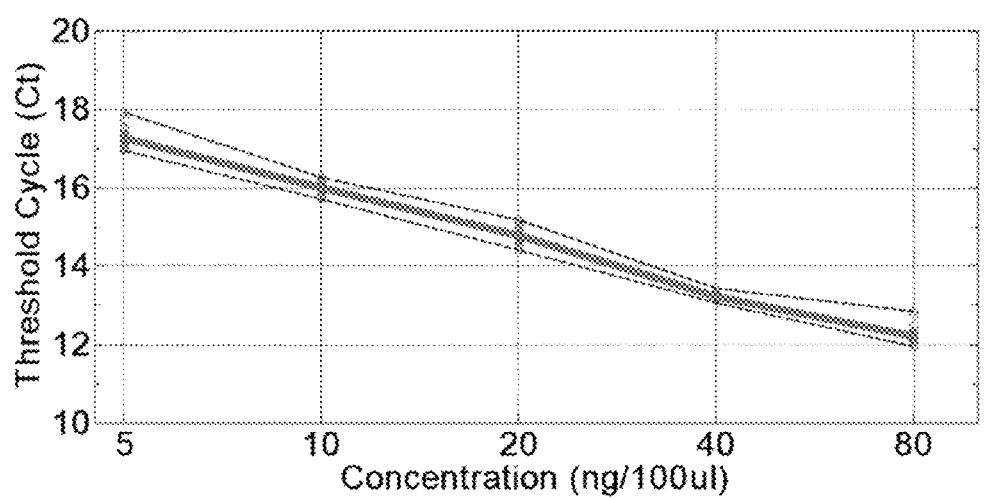
FIG. 18 shows signal measured in an example array.

With methods and systems provided herein, the amplification reaction can be monitored in real-time (FIG. 17) and a correlation or association between threshold cycle ($C_t$) and template concentration can be identified (FIG. 18).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for assaying at least one target nucleic acid molecule, comprising:
   (a) providing a reaction mixture comprising a nucleic acid sample containing at least one template nucleic acid molecule, a primer pair and a polymerase, wherein said primer pair has sequence complementarity with said template nucleic acid molecule, and wherein said primer pair comprises a limiting primer and an excess primer;
   (b) subjecting said reaction mixture to a nucleic acid amplification reaction under conditions that are sufficient to yield said at least one target nucleic acid molecule as an amplification product of said template nucleic acid molecule and said limiting primer, which at least one target nucleic acid molecule comprises said limiting primer;
   (c) bringing said reaction mixture in contact with a sensor array having (i) a substrate comprising a plurality of probes immobilized to a surface of said substrate at different individually addressable locations, wherein said probes have sequence complementarity with said limiting primer and are capable of capturing said limiting primer, and (ii) an array of detectors configured to detect at least one signal from said addressable locations, wherein said at least one signal is indicative of said limiting primer binding with an individual probe of said plurality of probes;
   (d) using said array of detectors to detect said at least one signal from one or more said addressable locations at multiple time points during said nucleic acid amplification reaction; and
   (e) detecting said target nucleic acid molecule based on said at least one signal indicative of said limiting primer binding with said individual probe of said plurality of probes.

2. The method of claim 1, wherein said at least one signal is produced upon binding of said probes to said limiting primer.

3. The method of claim 1, wherein said reaction mixture comprises a plurality of limiting primers having different nucleic acid sequences, and said probes specifically bind to said plurality of said limiting primers.

4. The method of claim 1, wherein said reaction mixture is provided in a reaction chamber configured to retain said reaction mixture and permit said probes to bind to said limiting primer.

5. The method of claim 1, further comprising correlating said detected at least one signal at multiple time points with an original concentration of said at least one template nucleic acid molecule by analyzing a binding rate of said probes with said limiting primer.

6. The method of claim 1, wherein said probes are oligonucleotides.

7. The method of claim 1, wherein said target nucleic acid molecule forms a hairpin loop when hybridized to an individual probe.

8. The method of claim 1, wherein said sensor array comprises at least about 100 integrated sensors.

9. The method of claim 1, wherein said at least one signal is an optical signal that is indicative of an interaction between an energy acceptor and an energy donor.

10. The method of claim 9, wherein said energy acceptor is coupled to said excess primer and/or said limiting primer.

11. The method of claim 9, wherein said energy acceptor is coupled to said target nucleic acid molecule.

12. The method of claim 9, wherein said energy acceptor is a quencher.

13. The method of claim 9, wherein said energy donor is a fluorophore.

14. The method of claim 1, wherein said at least one signal is an electrical signal that is indicative of an interaction between an electrode and a redox label.

15. The method of claim 14, wherein said redox label is coupled to said excess primer and/or said limiting primer.

16. The method of claim 14, wherein said redox label is coupled to said target nucleic acid molecule.

17. The method of claim 1, wherein (d) comprises measuring an increase in said at least one signal relative to background.

18. The method of claim 1, wherein (d) comprises measuring a decrease in said at least one signal relative to background.

19. The method of claim 1, wherein said target nucleic acid molecule is detected at a sensitivity of at least about 90%.

20. The method of claim 1, wherein said at least one signal is detected while said reaction mixture comprising said target nucleic acid molecule is in fluid contact with said sensor array.

21. A system for assaying at least one target nucleic acid molecule, comprising:
   (a) a reaction chamber comprising a reaction mixture comprising a nucleic acid sample containing at least one template nucleic acid molecule, a primer pair that has sequence complementary to said template nucleic acid molecule, and a polymerase, wherein said primer pair comprises a limiting primer and an excess primer, wherein said reaction chamber comprising said reaction mixture is configured to facilitate a nucleic acid amplification reaction on said reaction mixture to yield at least one target nucleic acid molecule as an amplification product of said template nucleic acid;
   (b) a sensor array comprising (i) a substrate comprising a plurality of probes immobilized to a surface of said substrate at different individually addressable locations, wherein said probes have sequence complementarity with said limiting primer and are capable of capturing said limiting primer; and (ii) an array of detectors configured to detect at least one signal from said addressable locations, wherein said at least one signal is indicative of said limiting primer binding with an individual probe of said plurality of probes; and
   (c) a computer processor coupled to said sensor array and programmed to (i) subject said reaction mixture to said nucleic acid amplification reaction, and (ii) detect said at least one signal from one or more of said addressable locations at multiple time points during said nucleic acid amplification reaction.

22. The method of claim 1, wherein (b) comprises generating a plurality of target nucleic acid molecules having sequence complementarity with said template nucleic acid.

23. The method of claim 22, wherein said array of detectors is configured to detect a plurality of signals from said addressable locations, wherein each of said plurality of signals is indicative of said limiting primer binding with an individual probe of said plurality of probes.

24. The method of claim 23, wherein (d) comprises using said array of detectors to detect a plurality of signals from said addressable locations at said multiple time points, wherein each of said plurality of signals is indicative of said limiting primer binding with an individual probe of said plurality of probes.

25. The method of claim 1, wherein (e) comprises identifying said limiting primer.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaactc tattcatctc ctagtagatc                                      30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 2
aaaaaaatca tactagccta tggacta                                          27
```